(12) United States Patent
Divincenzo et al.

(10) Patent No.: US 9,855,087 B2
(45) Date of Patent: Jan. 2, 2018

(54) METHODS AND DEVICES FOR SPINAL SCREW INSERTION

(71) Applicant: DePuy Synthes Products, LLC, Raynham, MA (US)

(72) Inventors: John Divincenzo, Weymouth, MA (US); Nicholas Pavento, North Attleboro, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 482 days.

(21) Appl. No.: 14/450,952

(22) Filed: Aug. 4, 2014

(65) Prior Publication Data

US 2016/0030100 A1 Feb. 4, 2016

(51) Int. Cl.
*A61B 17/88* (2006.01)
*A61B 17/70* (2006.01)

(52) U.S. Cl.
CPC ...... *A61B 17/8875* (2013.01); *A61B 17/7082* (2013.01); *A61B 17/7091* (2013.01)

(58) Field of Classification Search
CPC .................................................. A61B 17/8875
See application file for complete search history.

(56) References Cited

U.S. PATENT DOCUMENTS

| | | | |
|---|---|---|---|
| 6,019,776 A | 2/2000 | Preissman et al. | |
| 6,402,757 B1 | 6/2002 | Moore, III et al. | |
| 6,736,820 B2 | 5/2004 | Biedermann et al. | |
| 6,827,722 B1 * | 12/2004 | Schoenefeld | A61B 17/1622 606/104 |
| 6,974,460 B2 | 12/2005 | Carbone et al. | |
| 6,981,974 B2 | 1/2006 | Berger | |
| 7,179,261 B2 | 2/2007 | Sicvol et al. | |
| 7,207,995 B1 * | 4/2007 | Vandewalle | A61B 17/8875 606/104 |
| 7,338,494 B2 | 3/2008 | Ryan | |
| 7,488,323 B2 | 2/2009 | Bacastow et al. | |
| 7,604,643 B2 | 10/2009 | Ciccone et al. | |
| 7,892,207 B2 | 2/2011 | Simonton et al. | |
| 7,938,836 B2 | 5/2011 | Ainsworth et al. | |
| 8,192,466 B2 | 6/2012 | Yue et al. | |
| 8,216,243 B2 | 7/2012 | Yevmenenko et al. | |
| 8,236,006 B2 | 8/2012 | Hamada | |
| 8,282,651 B2 | 10/2012 | Ciccone et al. | |
| 8,303,601 B2 | 11/2012 | Bandeira et al. | |
| 8,372,076 B2 | 2/2013 | Simonton et al. | |

(Continued)

*Primary Examiner* — David Bates
(74) *Attorney, Agent, or Firm* — Mintz Levin Cohn Ferris Glovsky and Popeo, P.C.

(57) ABSTRACT

Surgical instruments and methods for delivering bone anchor assemblies into bone are disclosed herein. Use of these anchors or instruments can eliminate one or more of the steps in a conventional bone anchor installation procedure, improving surgical efficiency and safety. In general, a surgical instrument can include a handle assembly having an elongate shaft extending distally therefrom. The handle assembly can be configured to axially translate a stylet extending therethrough relative to a bone anchor assembly coupled to the elongate shaft, and it can be configured to move the stylet proximally in response to distal advancement of a bone anchor assembly into bone. The surgical instruments can include various mechanisms for adjusting the position of the stylet.

26 Claims, 21 Drawing Sheets

(56) References Cited

U.S. PATENT DOCUMENTS

| | | |
|---|---|---|
| 8,394,108 B2 | 3/2013 | McLean et al. |
| 8,641,717 B2 * | 2/2014 | Defossez ............ A61B 17/8872 |
| | | 606/86 R |
| 8,715,293 B2 | 5/2014 | Vandewalle |
| 9,289,249 B2 * | 3/2016 | Ramsay ............. A61B 17/7076 |
| 2005/0216027 A1 | 9/2005 | Suh et al. |
| 2006/0079903 A1 | 4/2006 | Wong |
| 2006/0129238 A1 * | 6/2006 | Paltzer .................... A61F 2/447 |
| | | 623/17.11 |
| 2007/0016219 A1 | 1/2007 | Levine |
| 2008/0147128 A1 | 6/2008 | Fritzinger |
| 2009/0275994 A1 | 11/2009 | Phan et al. |
| 2010/0114174 A1 | 5/2010 | Jones et al. |
| 2010/0241124 A1 | 9/2010 | Housman et al. |
| 2011/0054537 A1 | 3/2011 | Miller et al. |
| 2011/0288599 A1 | 11/2011 | Michielli et al. |
| 2013/0012954 A1 | 1/2013 | Paroth et al. |
| 2013/0053901 A1 | 2/2013 | Cormier et al. |
| 2013/0096618 A1 | 4/2013 | Chandanson et al. |
| 2013/0310842 A1 * | 11/2013 | Winkler ............. A61B 17/8875 |
| | | 606/104 |
| 2014/0276892 A1 * | 9/2014 | Pakzaban ........... A61B 17/8875 |
| | | 606/104 |
| 2015/0201985 A1 * | 7/2015 | Rampersaud ...... A61B 17/8875 |
| | | 606/86 A |

* cited by examiner

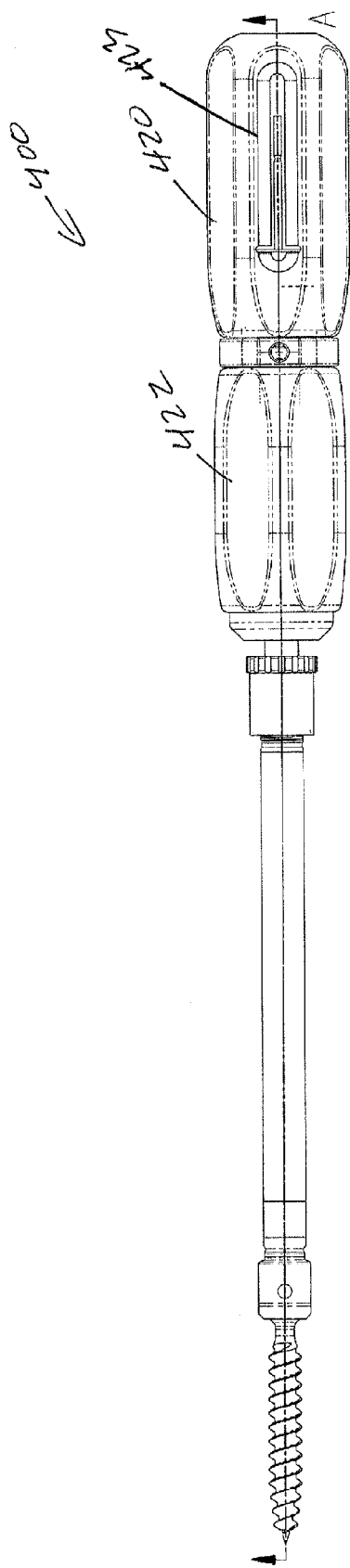
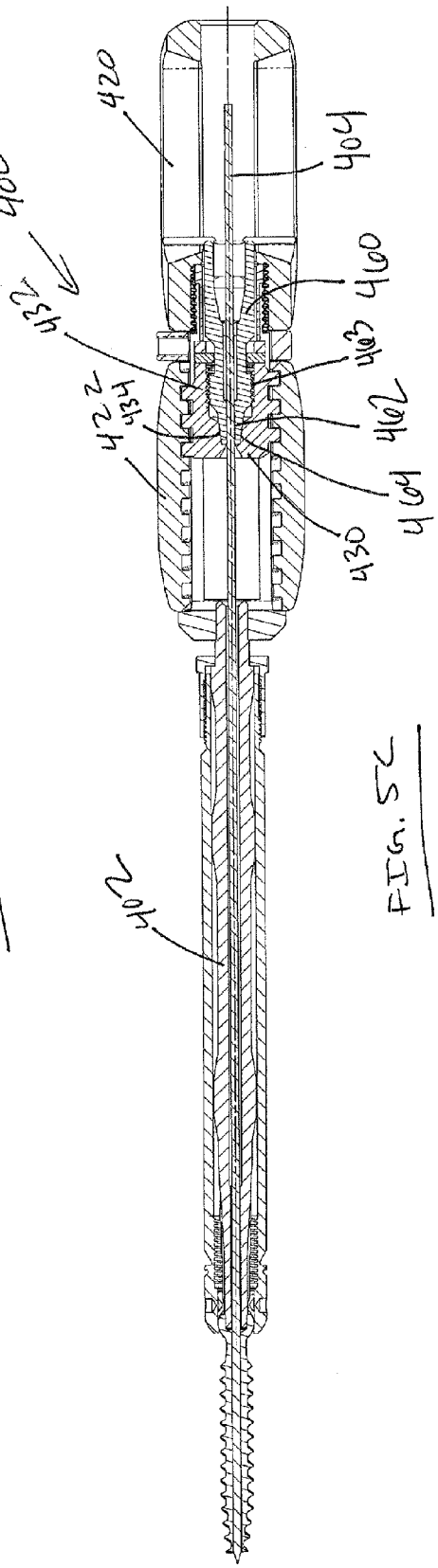
FIG. 5B
FIG. 5C
SECTION A-A

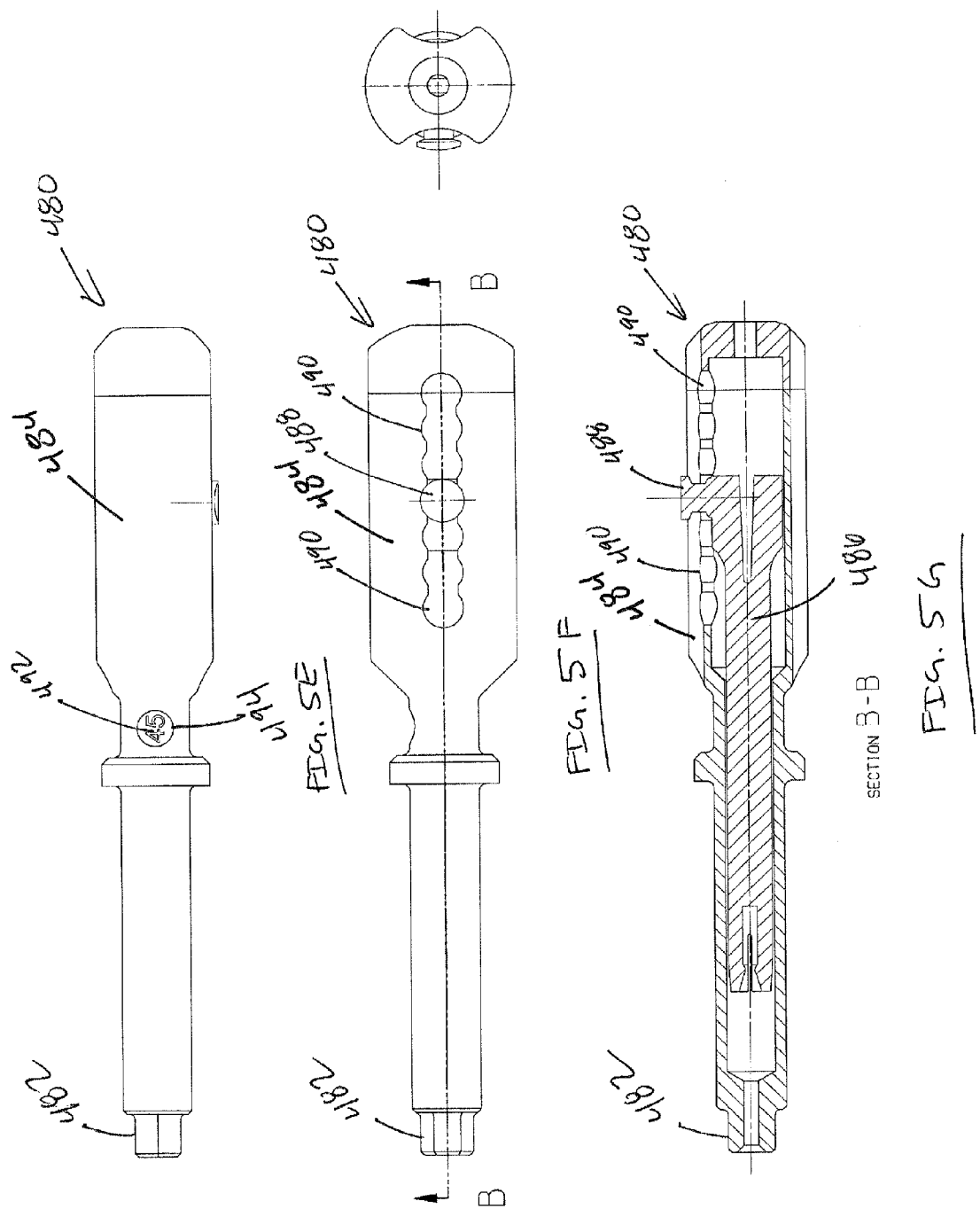

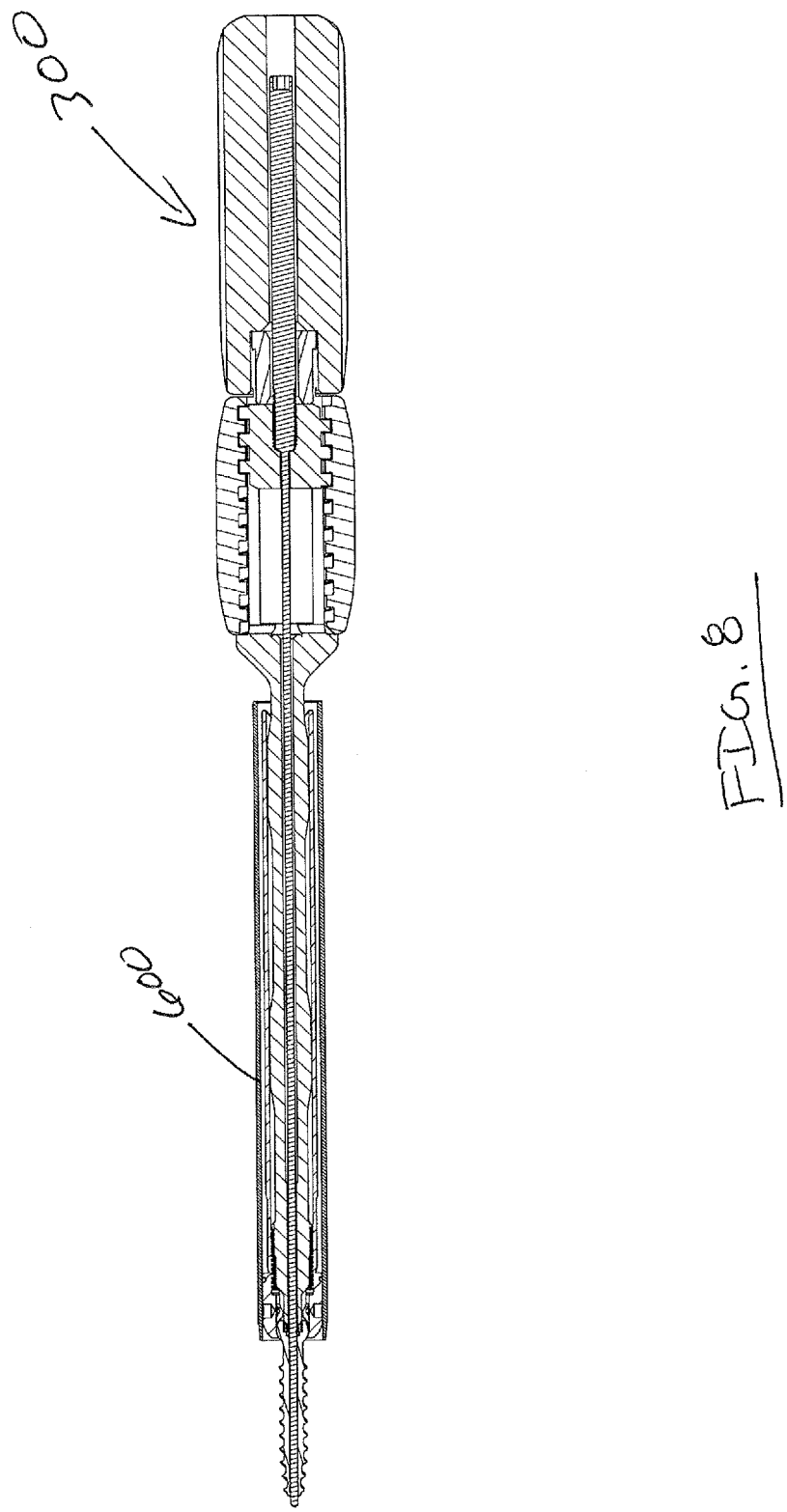

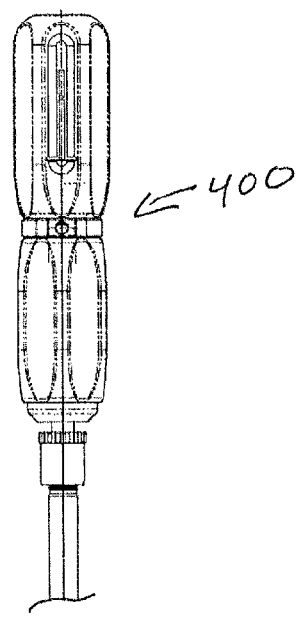
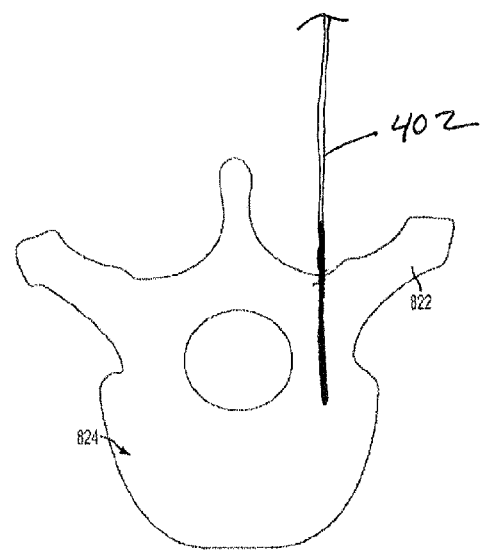
FIG. 10B

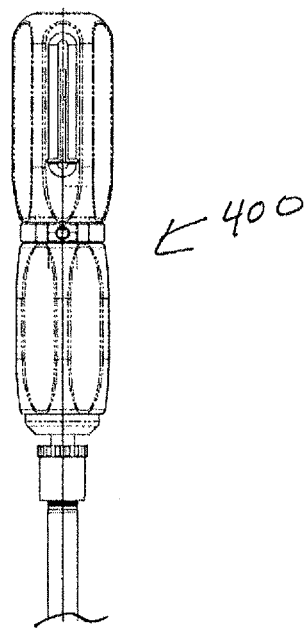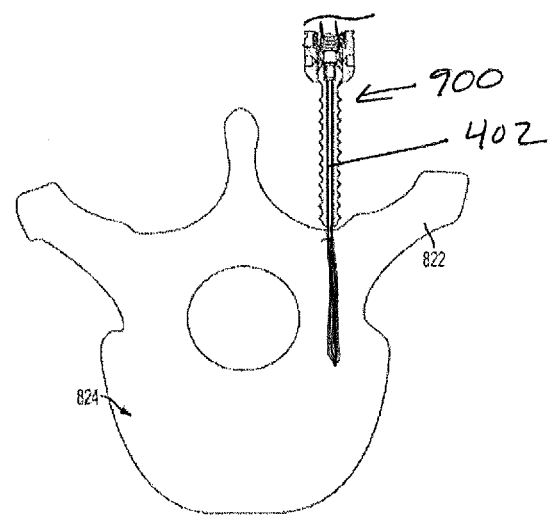
FIG. 10D

METHODS AND DEVICES FOR SPINAL SCREW INSERTION

FIELD

Bone anchors and associated instrumentation and methods are disclosed herein.

BACKGROUND

Bone anchors can be used in orthopedic surgery to fix bone during healing, fusion, or other processes. In spinal surgery, for example, bone anchors can be used to secure a spinal fixation element to one or more vertebrae to rigidly or dynamically stabilize the spine.

In a conventional procedure for coupling a bone anchor to bone, access to the bone is obtained, for example by forming a skin incision and resecting soft tissue disposed over the bone or by using a minimally-invasive technique. An insertion needle with a stylet disposed therein, sometimes referred to as a Jamshidi needle, is then driven into the bone to establish the trajectory for a bone opening. Next, the stylet is removed and a guidewire is inserted through the needle. The needle is then withdrawn over the guidewire, leaving the guidewire in place. A cannulated tap is then advanced over the guidewire and driven into the bone to enlarge the bone opening into a pilot hole for the bone anchor. Thereafter, the tap is withdrawn over the guidewire, again leaving the guidewire in place within the bone opening. A cannulated bone anchor is then advanced over the guidewire and driven into the bone opening. Finally, the guidewire is removed and one or more fixation elements are coupled to the bone anchor.

The conventional procedure detailed above suffers from a number of disadvantages. For example, the process involves several steps which can be time-consuming and cumbersome, particularly where a number of bone anchors are being installed. In addition, many of these steps (e.g., advancing the needle, advancing the guidewire, advancing the tap, and advancing the bone anchor) are done with fluoroscopic guidance to confirm the correct trajectory and insertion depth. With each additional step, the radiation exposure to the patient and surgical team increases, potentially causing dangerous complications or negative long-term health effects. The steps of removing the needle and removing the tap can also cause the guidewire to dislodge from the bone opening, requiring the process to be started anew. Further still, advancing the anchor or advancing the tap can inadvertently cause the guidewire to advance within the bone opening, potentially damaging delicate anatomical structures disposed in proximity to the bone. Advancing the anchor or advancing the tap can also cause the guidewire to become kinked, making removal of the guidewire very difficult. Accordingly, a need exists for improved bone anchors and associated instrumentation and methods.

SUMMARY

Various surgical instruments and methods are disclosed herein for implanting a bone anchor into bone. In one embodiment, a surgical instrument for driving a bone anchor assembly into bone is provided and includes an elongate shaft having a distal tip configured to couple to a bone anchor assembly, a handle assembly coupled to a proximal end of the shaft, and a stylet extending through an inner lumen of the handle assembly and the elongate shaft. The surgical instrument can further include a carrier disposed within the handle assembly, with the carrier being configured to non-rotatably translate relative to the elongate shaft in a proximal direction through the handle assembly to move the stylet proximally when the elongate shaft is rotated in order to drive a bone anchor assembly into bone.

The handle assembly can include a first and a second handles rotatably coupled to one another. Rotation of the first handle while the second handle is held stationary can cause the carrier to non-rotatably translate axially relative to the elongate shaft. Rotation of the second handle while the first handle is held stationary can cause the carrier to rotatably translate relative to the first handle. In some embodiments, the first handle can be positioned distal to the second handle. The surgical instrument can further include a stylet holder coupled to the carrier and releasably engaged to the stylet. The stylet holder can be releasably engaged with the carrier and can allow axial translation of the stylet when the stylet holder is in a first position relative to the carrier, and can prevent axial translation of the stylet when the stylet holder is in a second position relative to the carrier. The surgical instrument can further include a bone anchor assembly matable to the distal tip of the elongate shaft and having threads formed thereon that define an insertion rate of the bone anchor assembly into bone. The carrier can be configured to translate within the handle assembly at a rate that is equal to the insertion rate of the bone anchor assembly.

In some embodiments, a surgical instrument for driving a bone anchor assembly into bone can include an elongate shaft having proximal and distal ends, a mating feature formed on the distal end that is configured to mate to a bone anchor assembly, and an inner lumen extending through the elongate shaft. A stylet can extend through the inner lumen of the elongate shaft. The surgical instrument can also include a proximal handle configured to rotate the elongate shaft to drive a bone anchor assembly coupled to the mating feature on the distal end of the elongate body into bone. In addition, the surgical instrument can include a distal handle rotatable relative to the proximal handle. The surgical instrument can further include a carrier threadably disposed within the handle assembly and configured to move axially relative to the elongate shaft in response to rotation of one of the proximal and distal handles relative to the other one of the proximal and distal handles in order to cause the stylet to translate axially relative to the elongate shaft.

In one embodiment, rotation of the proximal handle while the distal handle is held stationary can cause rotation of the elongate shaft, and rotation and axial translation of the carrier within the handle assembly. Conversely, rotation of the distal handle while the proximal handle is held stationary can cause the carrier to translate axially within the handle assembly without rotating the elongate shaft. In certain embodiments, the proximal handle can be mated to the proximal end of the elongate shaft, and the distal handle can be rotatably disposed about a proximal portion of the elongate shaft at a location distal to the proximal handle. The carrier can be threadably coupled to threads formed within the distal handle and the stylet can be integrally formed on and can extend distally from the carrier. Alternatively or in addition, the stylet can be removably mated to the carrier by a mating element.

In certain embodiments, the surgical instrument can include a stylet holder disposed within the handle assembly that can allow the stylet to extend therethrough. The stylet holder can have a first position, in which the stylet is freely slidable relative to the stylet holder, and a second position in which the stylet holder rigidly engages the stylet to prevent movement of the stylet relative to the stylet holder. The stylet holder can be configured to be advanced into the carrier to cause the stylet holder to move from the first position to the second position. The stylet holder can include a clamping feature that is compressed by the carrier in the second position to cause the clamping feature to rigidly engage the stylet.

In other aspects, the elongate shaft of the surgical instrument can include a proximal portion with one or more slots, with the proximal portion extending through the distal handle and having a proximal end mated to the proximal handle. The carrier can be slidably disposed within the proximal portion, and the carrier can be non-rotatable relative to the proximal portion such that the carrier and the elongate shaft rotate together. The carrier can include one or more threaded features that extend through the one or more slots. The one or more slots can allow translation while preventing rotation of the carrier within the elongate shaft.

The surgical instrument can include other components, such as a protective sleeve removably disposed around the elongate shaft, and/or a positioning handle coupled to a proximal end of the stylet that is configured to adjust a length of stylet that extends from a bone anchor assembly coupled to the distal end of the elongate shaft. The positioning handle can include a tool feature for engaging a stylet holder disposed within the handle assembly and having the stylet extending therethrough. The tool feature can be configured to advance the stylet holder into the carrier to cause the stylet holder to move from a first position to a second position, wherein the second position locks the stylet to the stylet holder. The positioning handle can include an outer housing encompassing at least a part of a positioning feature that secures the proximal end of the stylet to the positioning handle. The positioning feature can include a push button that releasably engages an engagement position along the outer housing. The positioning feature can be configured to move with the stylet relative to the outer housing when the push button is disengaged from the engagement position.

In some embodiments, a surgical instrument for driving a bone anchor assembly into bone can include an elongate shaft having proximal and distal ends, a mating feature formed on the distal end and configured to mate to a bone anchor assembly, an inner lumen extending through the elongate shaft, and a handle assembly coupled to the elongate shaft. The handle assembly can include a distal handle coupled to the proximal end of the elongate shaft and it can be configured to rotate the elongate shaft to drive a bone anchor assembly coupled to the mating feature on the distal end of the elongate body into bone. The handle assembly can further include a proximal handle threadably coupled to the distal handle and coupled to a proximal end of a stylet that extends through the inner lumen of the elongate shaft, with the proximal handle being rotatable relative to the distal handle in order to cause the stylet to axially translate relative to the elongate shaft.

In some embodiments, a method of delivering a bone anchor assembly is provided. The method can include coupling an engagement portion on a shaft of a driver to a corresponding engagement portion on a bone anchor assembly. The method can also include rotating a second handle of the driver while holding a first handle of the driver stationary to cause a carrier disposed within the driver to translate a stylet relative to the bone anchor assembly. The method can further include rotating a first handle of the driver while holding a second handle of the driver stationary to cause the shaft to rotate and advance the bone anchor assembly along the stylet. When the first handle is rotated while the second handle is held stationary, the carrier can be caused to translate axially within the driver to move the stylet axially relative to the elongate shaft.

The present disclosure further provides devices and methods as claimed.

BRIEF DESCRIPTION OF THE DRAWINGS

The invention will be more fully understood from the following detailed description taken in conjunction with the accompanying drawings, in which:

FIG. 5B is a side view of the surgical instrument of FIG. 5A with a bone anchor assembly coupled to a distal end of an elongate shaft of the surgical instrument;

FIG. 5C is a cross-sectional view of the surgical instrument and bone anchor assembly of FIG. 5B;

FIG. 5E is a side view of the positioning handle of FIG. 5D showing a window in an outer body of the positioning handle revealing a marking;

FIG. 5F is a top view of the positioning handle of FIG. 5D showing a push button for adjusting a position of a stylet;

FIG. 5G is a cross-sectional view of the positioning handle of FIG. 5D showing a positioning feature within the outer body of the positioning handle.

FIG. 8 is a cross-sectional view of a protective sleeve positioned over a part of the elongate shaft of surgical instrument shown in FIG. 4;

FIGS. 10A-10D schematically illustrate a method of using the positioning handle and surgical instrument of FIGS. 5A-5G to drive a bone anchor assembly into bone.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Methods and devices for inserting bone anchor assemblies into bone are provided herein. Use of these anchors or instruments can eliminate one or more of the steps in a conventional bone anchor installation procedure, improving surgical efficiency and safety. In general, surgical insertion devices are provided that include a proximal handle and a distal handle, with the proximal handle configured to control the movement of an elongate shaft of the device and the distal handle configured to control the movement of a guidewire or stylet extending through the device. For example, rotation of the distal handle relative to the proximal handle can cause the stylet to axially translate in a proximal or distal direction relative to the elongate shaft. In addition, rotation of the proximal handle relative to the distal handle can cause the elongate shaft to rotate, which can assist with driving a bone anchor assembly coupled to a distal end of the elongate shaft into bone. We note that the terms guidewire and stylet are used interchangeably herein, and any configuration of a guidewire or stylet can be used with the various instruments and methods disclosed herein.

Prior Art Bone Anchor Assembly

Figure 1A:
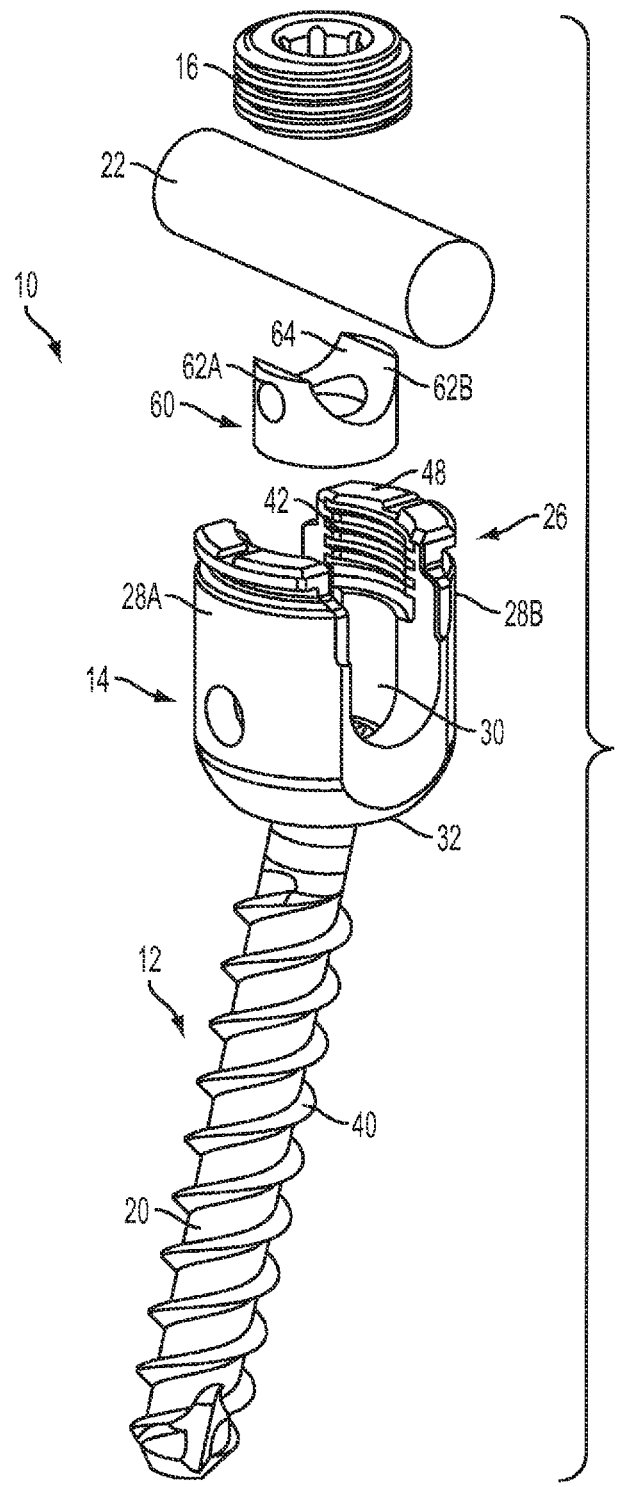
FIG. 1A is an exploded perspective view of a prior art bone anchor assembly.
Figure 1B:
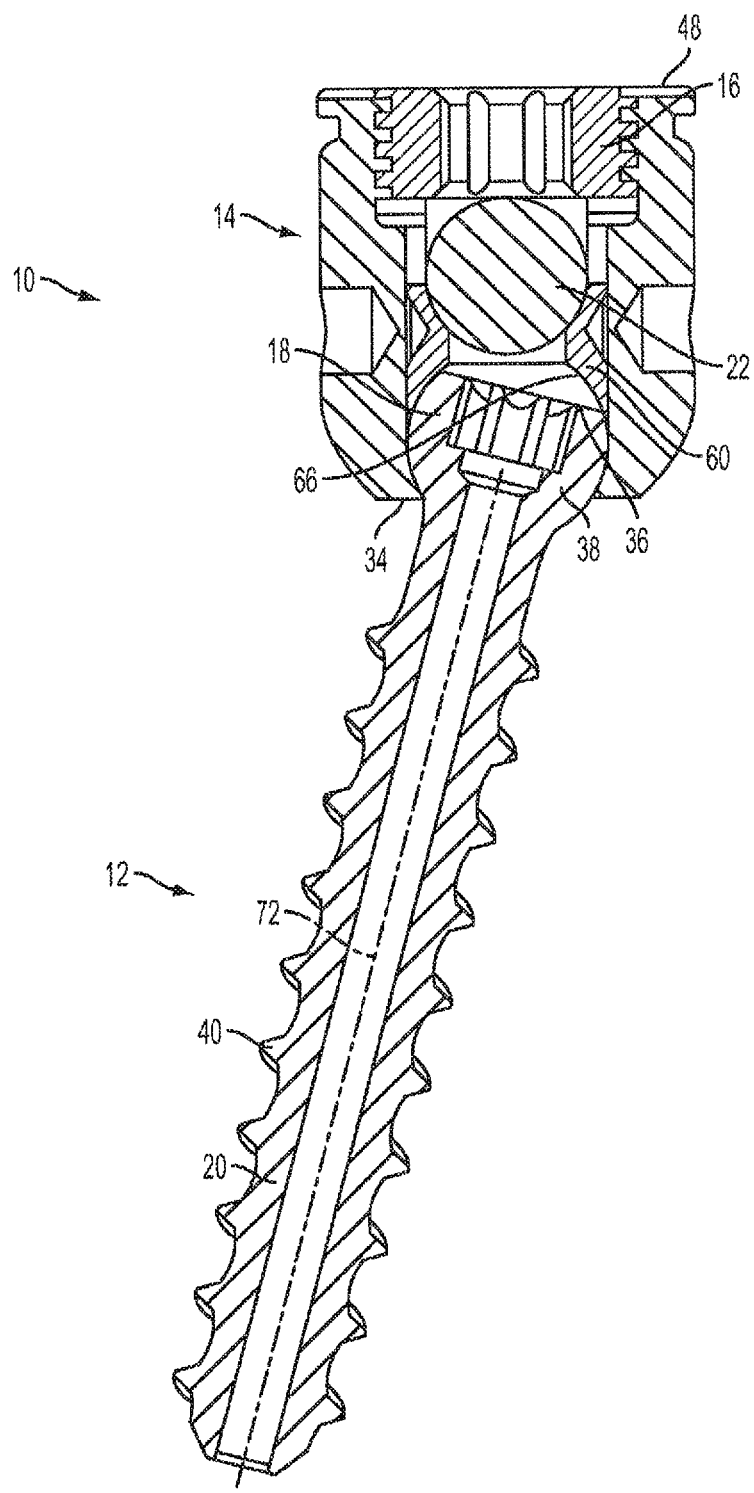
FIG. 1B is a sectional view of the prior art bone anchor assembly of FIG. 1A.

FIGS. 1A-1B illustrate one embodiment a prior art bone anchor assembly 10 that includes a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone screw designed for posterior implantation in the pedicle or lateral mass of a vertebra. The proximal head 18 of the bone anchor 12 engages the distal end 32 of the receiver member 14 in a ball and socket like arrangement in which the proximal head 18 and the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. While a threaded distal shaft 20 is shown, the distal shaft can have other structures for engaging bone, including a hook. The distal shaft 20 of the bone anchor 12 can be cannulated, having a central passage or inner lumen 72 extending the length of the bone anchor to facilitate delivery of the bone anchor over a guidewire or stylet in, for example, minimally-invasive procedures. Other components of the bone anchor assembly 10, including, for example, the closure mechanism 16, the receiver member 14, and the compression member 60 (discussed below), can be cannulated or otherwise have an opening to permit delivery over a guidewire or stylet. The distal shaft 20 can also include one or more sidewall openings or fenestrations that communicate with the inner lumen 72 to permit bone in-growth or to permit the dispensing of bone cement or other materials through the bone anchor 12. The sidewall openings can extend radially from the inner lumen 72 through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated by reference herein. The distal shaft 20 of the bone anchor 12 can also be coated with materials to permit bone growth, such as, for example, hydroxyapatite, and the bone anchor assembly 10 can be coated partially or entirely with anti-infective materials, such as, for example, tryclosan.

The receiver member 14, which couples to the bone anchor 12, includes a pair of spaced apart arms 28A, 28B at the proximal end 26 defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated by reference herein.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The bone anchor 10 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly can be a conventional (non-biased) polyaxial screw in which the bone anchor pivots in the same amount in every direction.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. The compression member 60 can include a pair of spaced apart arms 62A and 62B defining a U-shaped seat 64 for receiving the spinal rod 22 and a distal surface 66 for engaging the proximal head 18 of the bone anchor 12.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In other embodiments, however, the closure mechanism 16 can include an outer set screw operable to act on the compression member 60 and an inner set screw operable to act on the rod 22.

The bone anchor assembly 10 can be used with a spinal fixation element such as rigid spinal rod 22. Alternatively, the spinal fixation element can be a dynamic stabilization member, such as a flexible or selectively flexible member, that allows controlled mobility between the instrumented vertebrae.

In use, the bone anchor assembly 10 can be assembled such that the distal shaft 20 extends through the opening in the distal end 32 of the receiver member 14 and the proximal head 18 of the bone anchor 12 is received in the distal end 32 of the receiver member 14. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A driver tool can extend through the compression member 60 and can be fitted with the bone anchor 12 to drive the bone anchor 12 into bone. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the closure mechanism 16 to move it within the recess 30 so as to force the spinal rod 22 into engagement with the compression member 60 and to in turn force the compression member 60 onto the proximal head 18 of the bone anchor 12, thereby fixing the spinal rod 22 relative to the receiver member 14 and locking the angular position of the bone anchor 12 relative to the receiver member 14.

The surgical instruments disclosed herein can be configured to operate in conjunction with bone anchor assemblies of the type described above or other types known in the art. As indicated above, it will be appreciated that the bone anchor assembly 200 can be a monoaxial screw, a polyaxial screw, a uniplanar screw, a bone hook, a favored-angle screw, and/or any of a variety of other bone anchor types known in the art. Further information on favored-angle screws can be found in U.S. patent application Ser. No. 13/648,184, filed on Oct. 9, 2012, which is hereby incorporated by reference herein.

Insertion Instruments

In general, various insertion instruments are provided for driving a bone anchor assembly into bone. The insertion instruments generally include a handle assembly and an elongate shaft extending distally therefrom for coupling to a bone anchor assembly. The instruments are configured to receive a stylet therethrough and the handle assembly is configured to control positioning of the stylet. In particular, the handle assembly can be configured to allow for adjustment of an axial position of the stylet relative to a bone anchor assembly coupled to the elongate shaft. The handle assembly can also be configured to move the stylet proximally relative to a bone anchor assembly during insertion of the bone anchor assembly into bone. Such movement of the stylet can occur automatically, in response to rotation of a portion of the handle to drive the bone anchor assembly into bone. Such a configuration is particularly advantageous as it will prevent further insertion of the stylet into bone during advancement of the bone anchor assembly. A person skilled in the art will appreciate that the instruments disclosed herein can have a variety of configurations, and that the various features disclosed in the various embodiments are interchangeable.

Figure 2A:
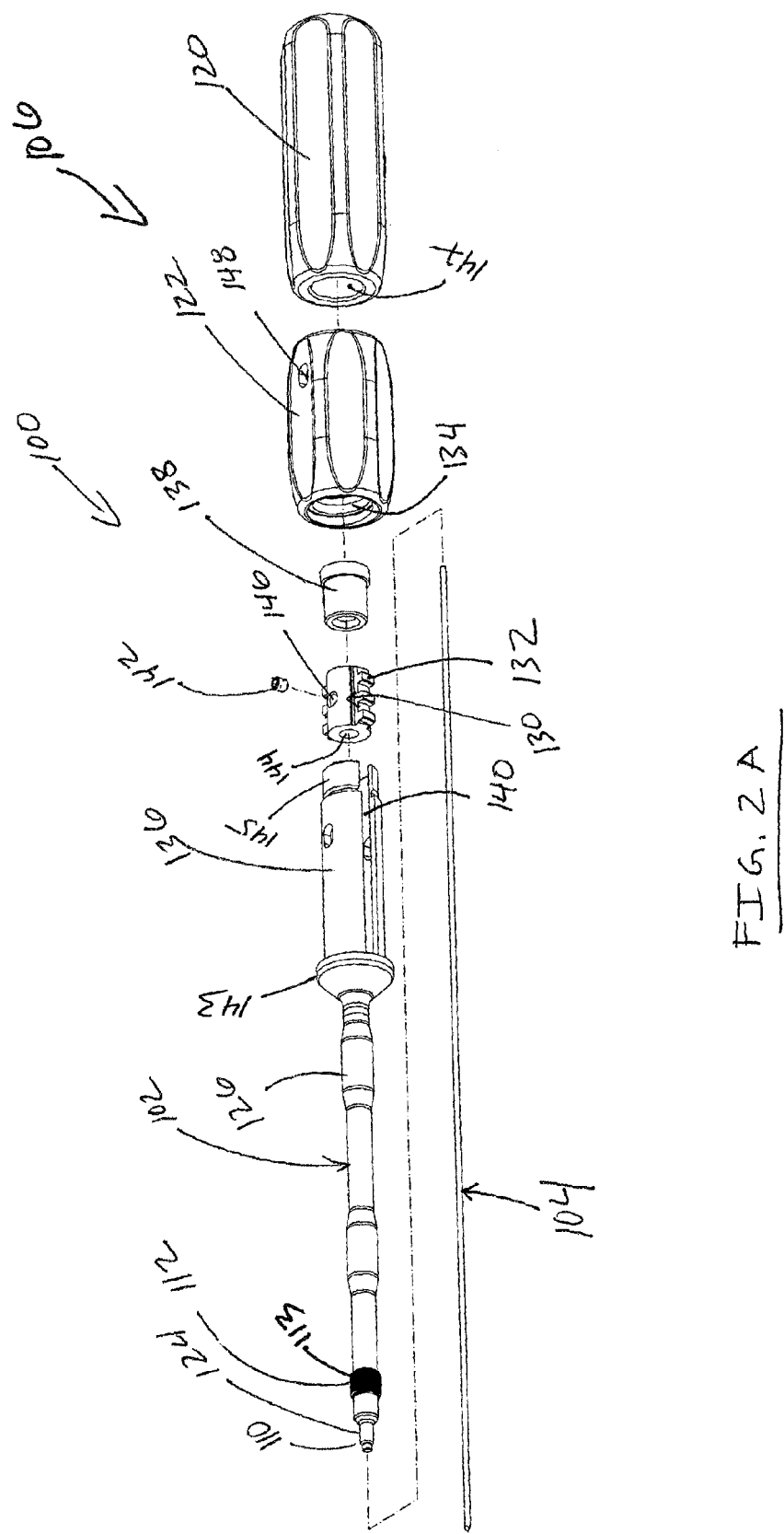
FIG. 2A is an exploded perspective view of one embodiment of a surgical instrument having a stylet that can be coupled to a carrier, the carrier and stylet can be axially translated as a result of rotating proximal and distal handles relative to one another.
Figure 2B:
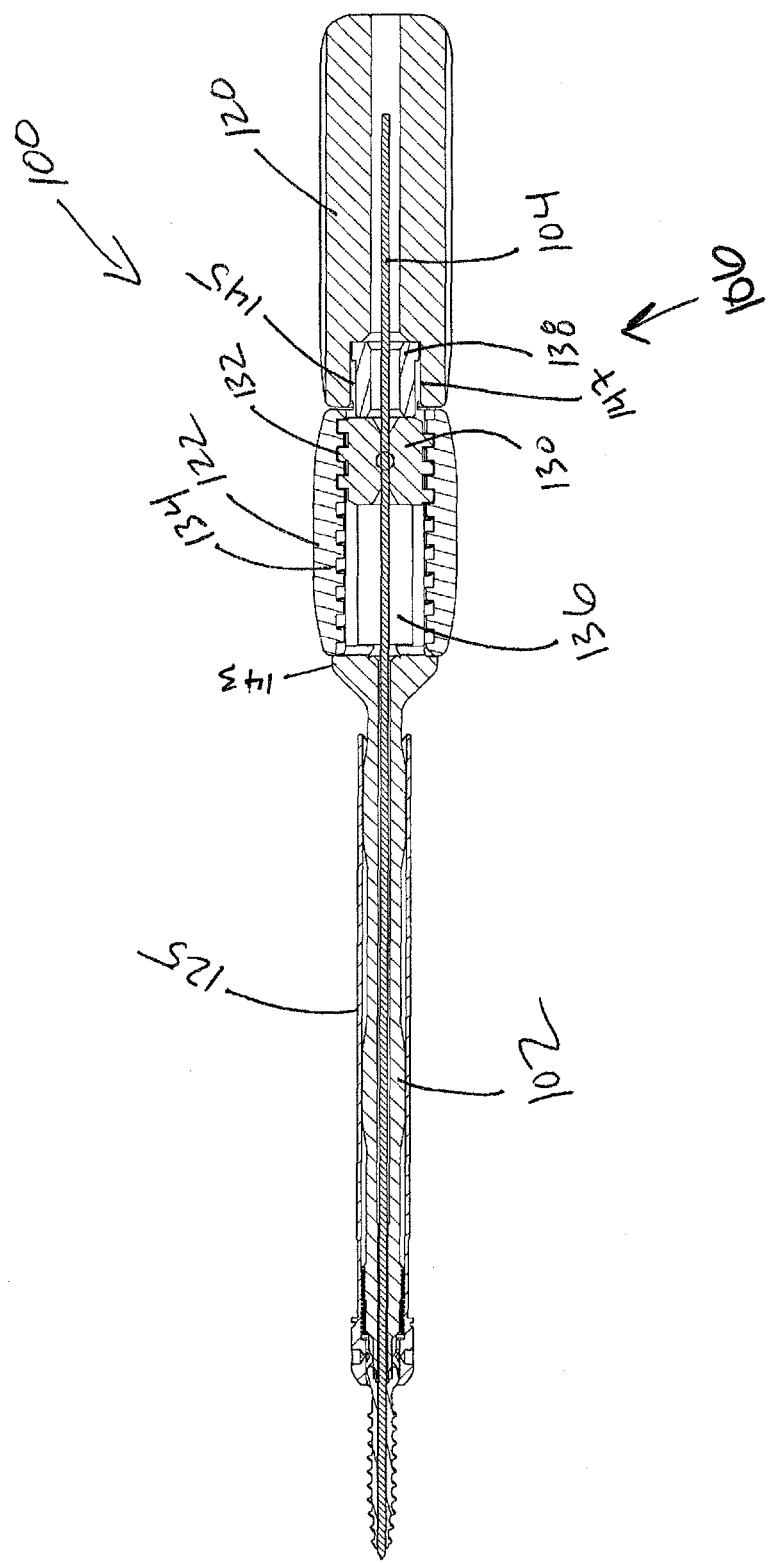
FIG. 2B is a cross-sectional view of the surgical instrument of FIG. 2A with a bone anchor assembly coupled to a distal end of an elongate shaft of the surgical instrument.

FIGS. 2A and 2B illustrate one exemplary embodiment of a surgical instrument 100 for driving a bone anchor assembly into bone. The surgical instrument can include a handle assembly 106 having an elongate shaft 102 extending distally therefrom, and a stylet 104 extending through the handle assembly 106 and the elongate shaft 102. The elongate shaft 102 can be configured to mate to a bone anchor assembly, and the handle assembly 106 can be configured to both drive a bone anchor assembly into bone, and manipulate the stylet both before and during insertion of a bone anchor assembly into bone.

The elongate shaft 102 can have a variety of configurations, but generally the shaft 102 includes a proximal end 108 for coupling to the handle assembly and a distal end 110 for mating to a bone anchor assembly. A length of the shaft 102 can vary, but the shaft preferably has a length sufficient to allow the handle assembly to be positioned outside of a patient's body while the distal end 110 is positioned into a patient's body adjacent to bone. To facilitate mating to a bone anchor assembly, the distal end 110 of the elongate shaft 102 can include a mating feature 112 formed thereon. The mating feature 112 can be formed anywhere along the elongate shaft 102, such as the distal end 110, and it can be configured to engage a bone anchor assembly (e.g., bone anchor assemblies of the type described above with respect to FIGS. 1A-1B). The mating feature 112 can include a threaded portion 113 configured to engage corresponding threads formed in the receiver member of the bone anchor assembly. The mating feature 112 can also include a tip 124 disposed distally of the threaded portion 113 and configured to engage a drive socket or a proximal surface of the bone anchor disposed within the receiver member. The tip 124 can have a diameter that is less than the diameter of the threaded portion 113. The mating feature 112 can also be configured to engage a bone tap, or a bone tap can be formed integrally with the elongate shaft 102. One or more bulges 126 or areas of increased diameter can be formed along the length of the elongate shaft 102 to engage and stabilize extension or protective sleeves that can be coupled to the bone anchor assembly. As shown in FIG. 2B, the bone anchor assembly can include break-off extensions 125, which can act as a delivery cannula during insertion of the set screw and can be broken off at the end of the procedure.

The elongate shaft 102 can include a cannulated proximal portion having a bore extending at least partially therethrough and one or more slots formed therein that define opposed tabs 136. The slot(s) can extend through only a portion of the proximal portion such that the opposed tabs 136 are connected at their proximal ends, or the slots extend through the entire length of the proximal portion as shown in the illustrated embodiment. A person skilled in the art will appreciate that the slots can have any length as may be required to allow for translation of the carrier, discussed below. In the illustrated embodiment, the tabs 136 can have a generally cylindrical configuration and define a hollow generally cylindrical interior lumen for receiving a carrier. A distal end of each tab 136 can be mounted on and can extend from a mounting surface defined by a proximal flange 143 formed on the elongate shaft, and a proximal end of each of the opposed tabs 136 can mate with a distal end of the proximal handle 120 such that rotation of the proximal handle 120 is effective to rotate the elongate shaft 102. In particular, the proximal end of each tab 136 can be sized to be received within a distal end of the proximal handle 120, as discussed below, and can be fixedly mated thereto, e.g., using an adhesive, welding, threads, or any other mating feature. In an exemplary embodiment, threads (not shown) are formed on an outer surface of the proximal end of the opposed tabs 136 for mating with corresponding threads formed within the proximal handle 120. Where the tabs are not connected, a support collar 138 can optionally be disposed within a proximal portion of the opposed tabs 136 to prevent inward radial movement of the opposed tabs and to maintain the threaded connection between the opposed tabs 136 and the proximal handle 120, as shown in FIG. 2B; however, one or more of a variety of features can be used to connect any part of the elongate shaft 102, such as the opposed tabs 136, to the proximal handle 120. In addition, although described herein as opposed tabs 136, the proximal end of the elongate shaft 102 can have a variety of configurations including various shapes and sizes. Preferably, the proximal end is in the form of a body having a lumen and at least one slot, with the shape of the body varying as may be determined based on the shape of the handle disposed therearound. Any number of a variety of features and configurations can be included at the proximal end of the elongate shaft 102 and are not limited to opposed tabs 136.

As indicated above, the handle assembly 106 can be located adjacent the proximal end 108 of the elongate shaft 102 and can include a proximal handle 120 and a distal handle 122. The handle assembly 106 can be positioned and sized to allow a user, such as a surgeon, to grasp a part of the handle assembly 106 and operate the surgical instrument 100. While the proximal and distal handles 120, 122 can each have a variety of configurations, in the illustrated embodiment each handle 120, 122 has a generally elongate cylindrical configuration and is cannulated with an inner lumen extending therethrough, as shown in FIG. 2B. Each handle 120, 122 can include gripping features, such as knurling or other surface features, formed thereon to facilitate grasping of the device. The proximal handle 120 can be coupled to the proximal end 108 of the elongate shaft 102 and can be configured to rotate the elongate shaft 102, such as to drive a bone anchor assembly coupled to the mating feature 112 into bone. In particular, as described above, threads or other mating features on a proximal end of the opposed tabs 136 can mate to threads 147 formed within a distal portion of the inner lumen of the proximal handle.

As shown in FIG. 2B, the inner lumen in the proximal handle 120 includes an enlarged diameter region along its distal portion for receiving a proximal-most end or extension 145 of the opposed tabs 136 at the proximal end of the elongate shaft 102. The distal handle 122 can be positioned just distal to the proximal handle 120 and can be moveably disposed about a proximal portion of the elongate shaft 102. In particular, as shown in FIG. 2B, the distal handle 122 can be disposed about the opposed tabs 136 of the elongate shaft 102 and can be configured to freely rotate relative to at least the elongate shaft 102. The proximal flange 143 on the elongate shaft 102 can assist in preventing translational movement of the distal handle 122 relative to the proximal handle 120 and elongate shaft 102. In order to facilitate mounting of the distal handle 122 about the opposed tabs 136, the inner lumen extending through the distal handle can have a diameter that is slightly larger than an outer diameter of the opposed tabs 136. As further shown in FIG. 2B, the distal handle 122 can include interior threads 134 formed therein and extending along at least a portion or an entire length of the inner lumen extending through the distal handle 122. The threads 134 can mate with threads on the carrier, as discussed below. In use, each of the proximal and distal handles 120, 122 can be rotated relative to one other while the other handle is held stationary. Rotation of the proximal handle 120 will rotate the shaft 102 to drive a bone anchor assembly into bone, and rotation of the distal handle 122 can assist with positioning the stylet 104 relative to the elongate shaft 102, such as to allow a length of stylet 104 to extend from the distal end 110 of the elongate shaft 102, as will be discussed in detail below.

Although described as the proximal handle 120 being configured to rotate the elongate shaft 102 and the distal handle 122 being configured to axially translate the stylet 104 relative to the elongate shaft 102, the proximal handle 120 can be configured to axially translate the stylet 104 relative to the elongate shaft 102 and the distal handle 122 can be configured to rotate the elongate shaft 102.

Continuing to refer to FIGS. 2A and 2B, the surgical instrument 100 can further include a carrier 130 movably disposed within the handle assembly 106. The carrier 130 can be configured to couple to a stylet, as discussed below, and in use the carrier can facilitate positioning of the stylet relative to a bone anchor assembly coupled to the elongate shaft 102.

While the carrier 130 can have a variety of configurations, in the illustrated embodiment the carrier 130 has a generally cylindrical configuration and is cannulated with an inner lumen extending therethrough. As shown in FIG. 2B, the carrier 130 can be slidably disposed within the opposed tabs 136. The carrier 130 can thus have an outer diameter that is less than an inner diameter of the lumen defined by the opposed tabs 136 to allow the carrier to be disposed therein. The carrier 130 can include one or more threaded features 132 formed on an outer surface of the carrier 130 that engage the interior threads 134 located on an inner surface of the distal handle 122. As shown in FIG. 2B, the carrier 130 includes first and second threaded features formed on opposed sides thereof and not extending fully circumferentially around the carrier, with the opposed threaded features being received within the opposed slots 140 in the opposed tabs 136. Thus a portion of the outer surface of the carrier 130 can be non-threaded and configured to slide along or adjacent the inner walls of the opposed tabs 136, such as when the carrier 130 translates and moves the stylet 104 in a proximal or distal direction. The one or more slots 140 can allow the one or more threaded features 132 formed on opposed sides of the carrier to extend therethrough and to engage the threaded features 134 of the distal handle 122. Such a configuration will allow the threaded features 134, and thus the carrier 130, to translate axially along the opposed tabs 136, yet will prevent rotation of the carrier relative to the opposed tabs 136, and thus the elongate shaft 102. As a result, when the proximal handle 120 is be held by the user and the distal handle 122 is rotated, the threads 134 in the distal handle 122 will interact with the threaded features 132 on the carrier 130 to cause the carrier 130 to translate axially without rotating along the opposed tabs 136 and relative to the elongate shaft 102. In addition, if the distal handle 122 is held and the proximal handle 120 is rotated, the opposed tabs 136, which rotate in coordination with the proximal handle 120, will force the carrier 130 to rotate. The interaction between the threads in the distal handle 122 and the threaded features 132 on the carrier will thus cause the carrier 130 to translate axially along the opposed tabs 136 and thus relative to the elongate shaft.

In some implementations, the thread pitch of the carrier 130 and distal handle 122 can be the same as the thread pitch of the bone screw. The direction of the threads in the carrier 130 and distal handle 122, however, are preferably reversed as compared to a direction of the threads on a bone-screw. Such a configuration can allow the bone screw to advance into the bone at approximately the same rate as the stylet is retracted, as discussed below. Reversal of the thread pitch also results in a configuration in which the proximal handle 120 can be rotated in a first direction, e.g., clockwise, to drive a bone screw into bone, while rotation of the distal handle in a second opposite direction, e.g. counter-clockwise, is effective to advance the carrier 130 and stylet distally through distal handle 122. In other embodiments, the thread pitch of the carrier 130 and distal handle 122 can differ from the thread pitch of the bone screw so as to result in movement of the stylet at a rate that is greater or less than a rate of insertion of the bone screw. In addition, the slots 140 can extend approximately 30 millimeters to approximately 60 millimeters. Thus, this can allow the carrier 130 and stylet 104 to translate a distance of approximately 30 millimeters to approximately 60 millimeters. However, the slots 140 can extend a variety of lengths and are not limited to the examples described herein.

Movement of the carrier 130 within the distal handle 122, as described above, can cause corresponding movement of a stylet coupled thereto. FIGS. 2A and 2B illustrate a stylet 104 having a generally elongate configuration with a pointed distal tip to facilitate insertion into bone. As noted above, the stylet 104 or guidewire can have a variety of configurations. As shown in FIGS. 2A and 2B, the carrier 130 can include an inner lumen 144 that extends along the length of the carrier 130 and is configured to allow the stylet 104 to extend through. The stylet 104 can be integrally formed on and can extend distally from the carrier 130, or it can be removably mated to the carrier, such as with the assistance of a mating element (e.g., set screw). For example, the mating element can allow the length of stylet 104 extending in a direction from the carrier 130 to be altered. In the illustrated embodiment, the carrier 130 can include a threaded thru-hole 146 extending radially through a sidewall thereof that can accept a set screw 142 that can be advanced into the carrier 130 in order to engage and secure the stylet 140 within the inner lumen 144 of the carrier. Additionally, the handle assembly 106, such as the distal handle 122, can include a thru-hole 148 that can allow a tool to be inserted through the thru-hole and to access the set screw for adjusting the axial position of the stylet 104 relative to the carrier 130. For example, adjusting the position of the stylet 104 relative to the carrier 130 can affect the length of stylet 104 that can extend from the distal end 110 of a bone anchor assembly coupled to the elongate shaft 102. For example, distal translation of the stylet 104 can allow the length of stylet extending from the distal end 110 of the elongate shaft 102 to increase and proximal translation of the stylet 104 can allow the length of stylet 104 extending from the distal end 110 of the elongate shaft 102 to decrease.

Figure 3:
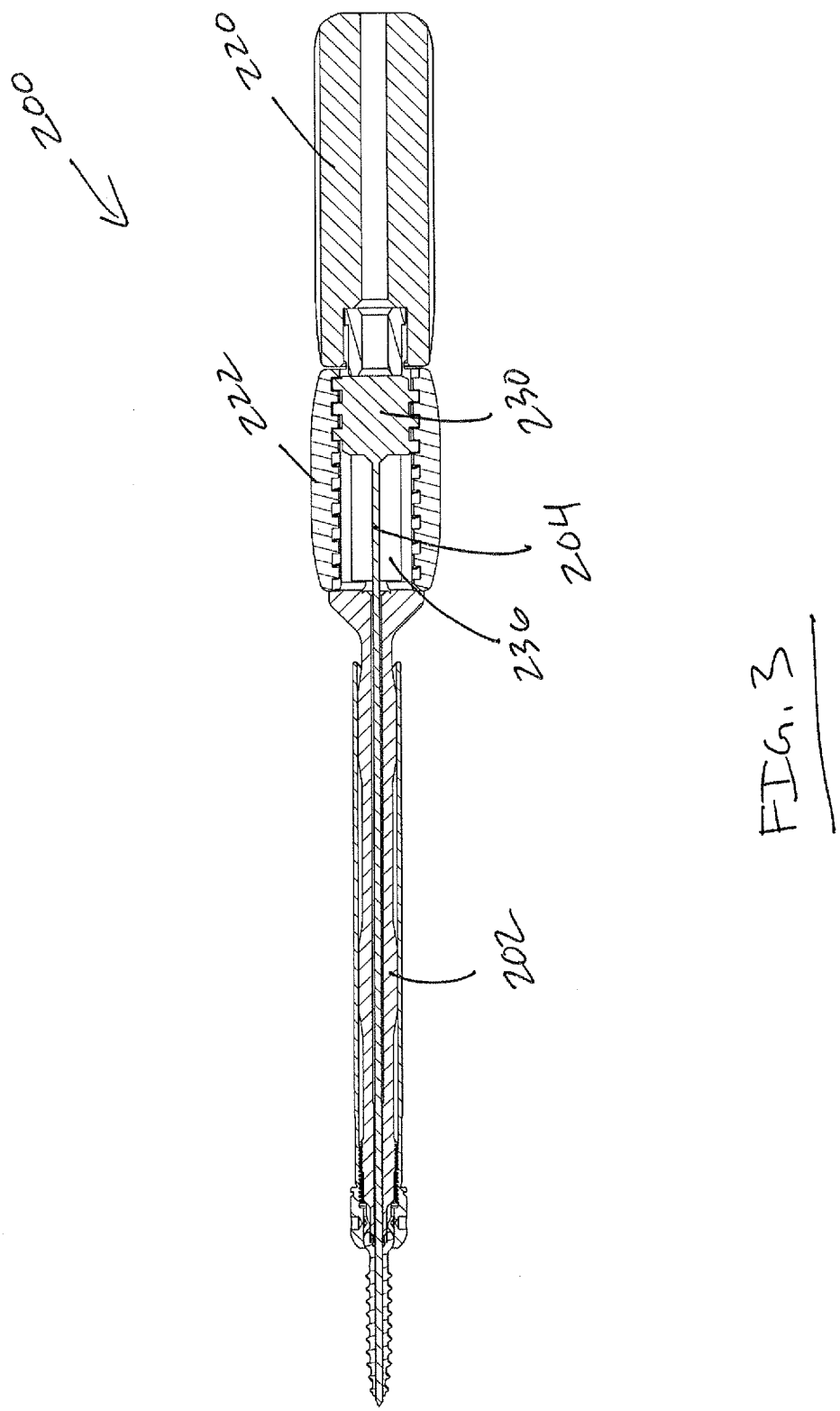
FIG. 3 is a cross-sectional view of another embodiment of a surgical instrument having a stylet integrated with and extending distally from a carrier.

FIG. 3 illustrates an embodiment of a surgical instrument 200 for driving a bone anchor assembly into bone that is identical to that of FIGS. 2A and 2B, except that the stylet 204 is integrally formed with the carrier 230. As shown in FIG. 3, the stylet 204 is unitary or monolithic with the carrier 230 and extends distally from a distal side of the carrier 230. In this embodiment, the stylet 204 can translate relative to the elongate shaft 202, but the stylet 204 cannot translate relative to the carrier 230. As such, the maximum length of stylet 204 that can extend from the distal end 210 of the elongate shaft 202 when the carrier 230 is in a most distal position relative to the distal handle 222 cannot be adjusted (i.e., lengthened or shortened).

Figure 4:
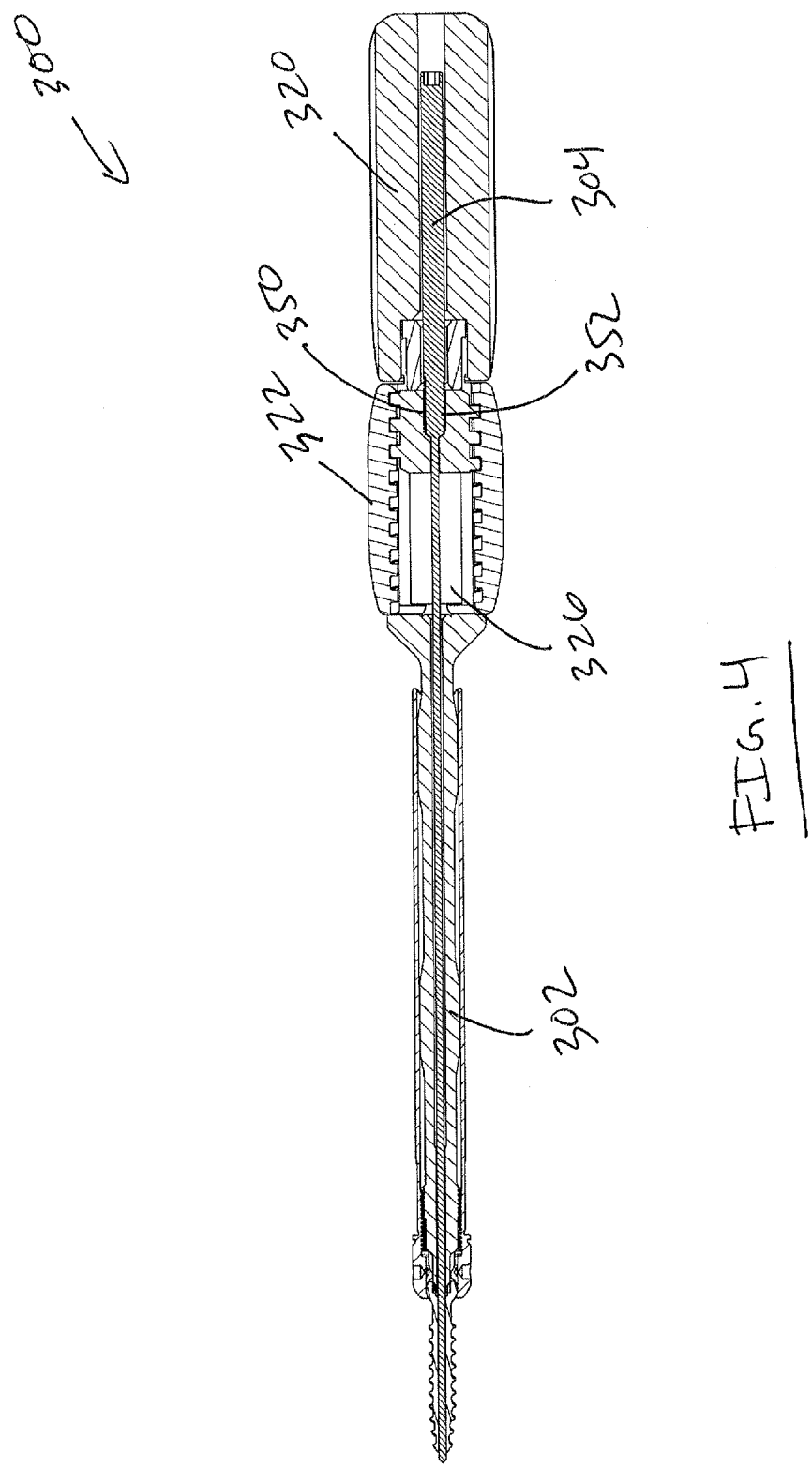
FIG. 4 is a cross-sectional view of yet another embodiment of a surgical instrument having a stylet threadably engaged with a carrier.

FIG. 4 illustrates another embodiment of a surgical instrument 300 for driving a bone anchor assembly into bone. The instrument 300 of FIG. 4 is identical to that of FIGS. 2A and 2B, except that the stylet 304 is threadably engaged with the carrier 330. For example, the stylet 304 can include threads 350 along a proximal portion of the stylet 304. In addition, the carrier 330 can include a thru-hole 352, with at least a part of the thru-hole including threads that can threadably engage the threads 350 along the stylet 304. Furthermore, the thru-hole 350 can either have more than one diameter (e.g., a recessed bore) or not be threaded all the way through, such as in order to prevent the stylet 304 from advancing too far through the carrier 330 or becoming disengaged. As such, the proximal end of the stylet 304 can be passed through the thru-hole 352 of the carrier 330 and the threaded portion 350 of the stylet 304 can be threadably engaged with the carrier 330 until the stylet 304 is secured to the carrier 330. Once the stylet 304 is secured to the carrier 330, such as during manufacturing of the surgical instrument, the stylet 304 can translate relative to the elongate shaft 302, but the stylet 304 cannot translate relative to the carrier 330. As such, the maximum length of stylet 304 that can extend from the distal end 310 of the elongate shaft 302 when the carrier 330 is in a most distal position relative to the distal handle 322 cannot be adjusted (i.e., lengthened or shortened).

FIGS. 5A-5G illustrate yet another embodiment of a surgical instrument 400 for driving a bone anchor into bone. The instrument 400 of FIGS. 5A-5G is identical to that of FIGS. 2A and 2B, except that the surgical instrument 400 includes a stylet holder 460 that can assist with coupling a stylet 404 to a carrier 430. The stylet holder 460 can include a thru-hole 462 along the length of the stylet holder 460 and the stylet 404 can extend through the thru-hole 462 in order to slidably engage with or secure to a part of the thru-hole 462. The stylet holder 460 can be loaded and/or removed from either the distal end or proximal end of the stylet holder. The engagement of the stylet 404 with the stylet holder 460 can depend on a positioning of the stylet holder 460 relative to the carrier 430, as will be described in greater detail below.

The stylet holder 460 can have a generally cylindrical configuration, although an outer diameter can vary along external portions thereof. As shown, the stylet holder 460 includes a proximal non-threaded cylindrical portion that is sized to be received within the support collar 438, and a distal portion having a threaded member 462 and a clamping feature 464. The distal portion is configured to be received within the carrier 430 such that the threaded member 462 formed along an outer surface of the stylet holder 460 is threadably engaged with a threaded bore 432 of the carrier 430. The clamping feature 464 is in the form of a slotted tapered nose defining opposed arms that are compressible radially inward to engage the stylet. The arms taper radially inward toward the distal-most end.

In use, the stylet holder 460 can be movable between a first position (unlocked) and a second position (locked) relative to the carrier 430. For example, in the first position, the stylet holder 460 can be, at most, partially threadably engaged with the carrier 430. In addition, when the stylet holder 460 is in the first position the clamping feature 464 of the stylet holder 460 is not engaged with the carrier. When the clamping feature 464 of the stylet holder 460 is not engaged with the carrier 430, the clamping feature 464 does not compress around the stylet 404 and allows the stylet 404 to be axially slidably moved within the stylet holder 460.

In the second position, the stylet holder 460 is fully threaded into the threaded bore 432 of the carrier 430 such that the clamping feature 464 of the stylet holder 460 is received within a tapered bore 434 formed in the carrier 430. When the clamping feature 464 of the stylet holder 460 is engaged with the tapered bore 434 of the carrier 430, the tapered bore 434 causes the arms of the clamping feature 464 to compress toward one another and around the stylet 404 such that the stylet holder 460 rigidly engages the stylet 404, thereby preventing axial translation of the stylet 404 independent of the stylet holder 460.

The stylet holder 460 can be advanced into the carrier 430 by the threaded engagement between the stylet holder 460 and the carrier 430. In addition, the stylet holder 460 can include a tool-engaging feature 466 (e.g., a recessed hex feature) that can allow a tool (e.g., a protruding hex feature) to engage and force the stylet holder 460 to rotate, such as relative to the carrier 430. For example, the stylet holder 460 can be forced to rotate in a first direction (e.g., clockwise) relative to the carrier 430 in order to move the stylet holder 460 to the second position. In addition, stylet holder 460 can be forced to rotate in a second direction (e.g., counterclockwise) relative to the carrier 430 in order to move the stylet holder 460 to the first position.

Figure 5A:
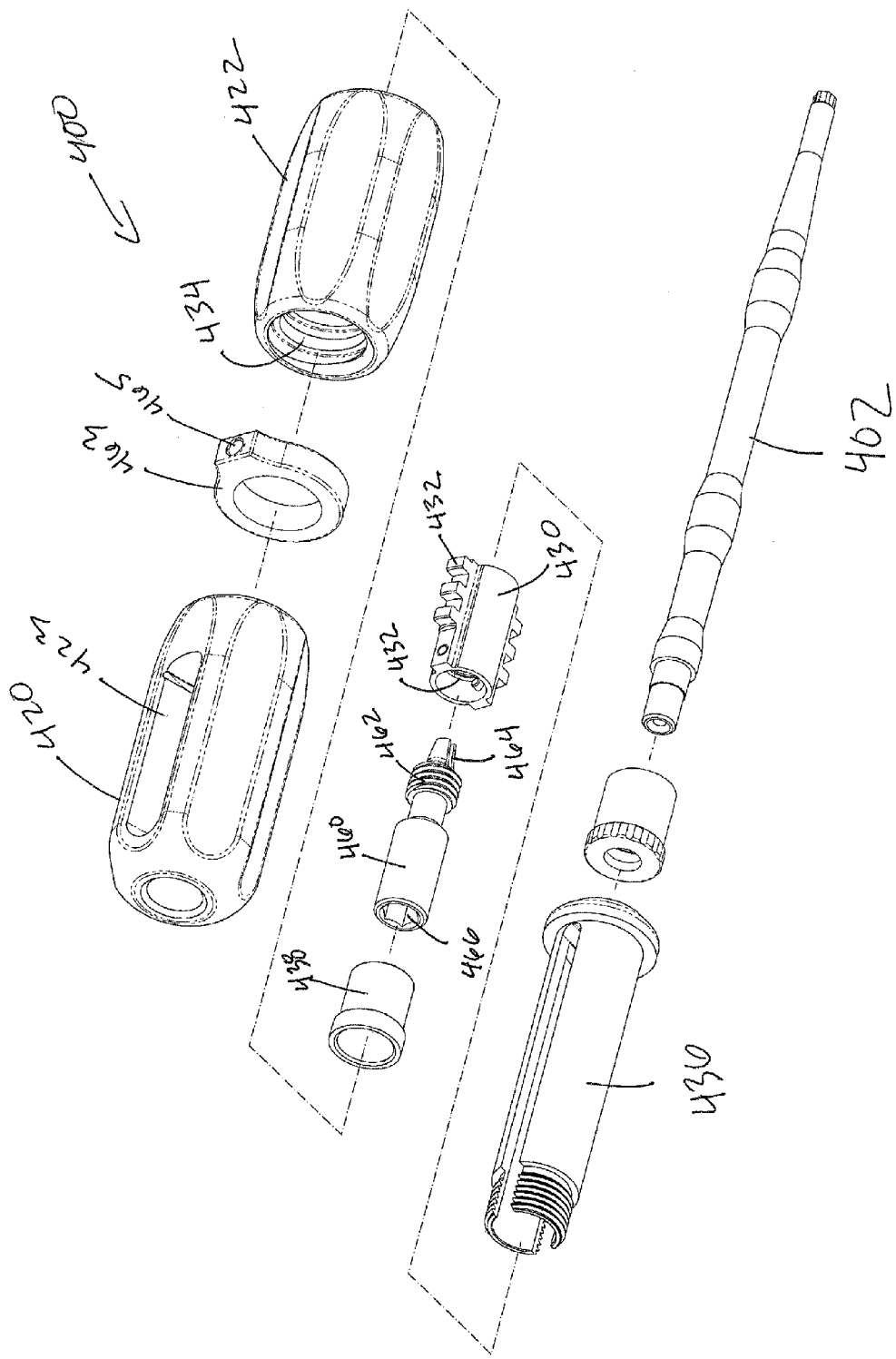
FIG. 5A is an exploded perspective view of a surgical instrument having proximal and distal handles and a stylet holder for carrying a stylet, according to another embodiment.

FIGS. 5A-5C further illustrate a ring 463 disposed between the proximal and distal handles 420, 422. The ring can be utilized with any of the embodiments disclosed herein, and acts as a holder for a positioning device, such as a three-dimensional sensor array for use in facilitating navigation during a surgical procedure. As show, the ring 463 is generally annular in shape and includes a bore 465, e.g., a threaded bore, formed therein for mating with a positioning device.

Figure 5D:
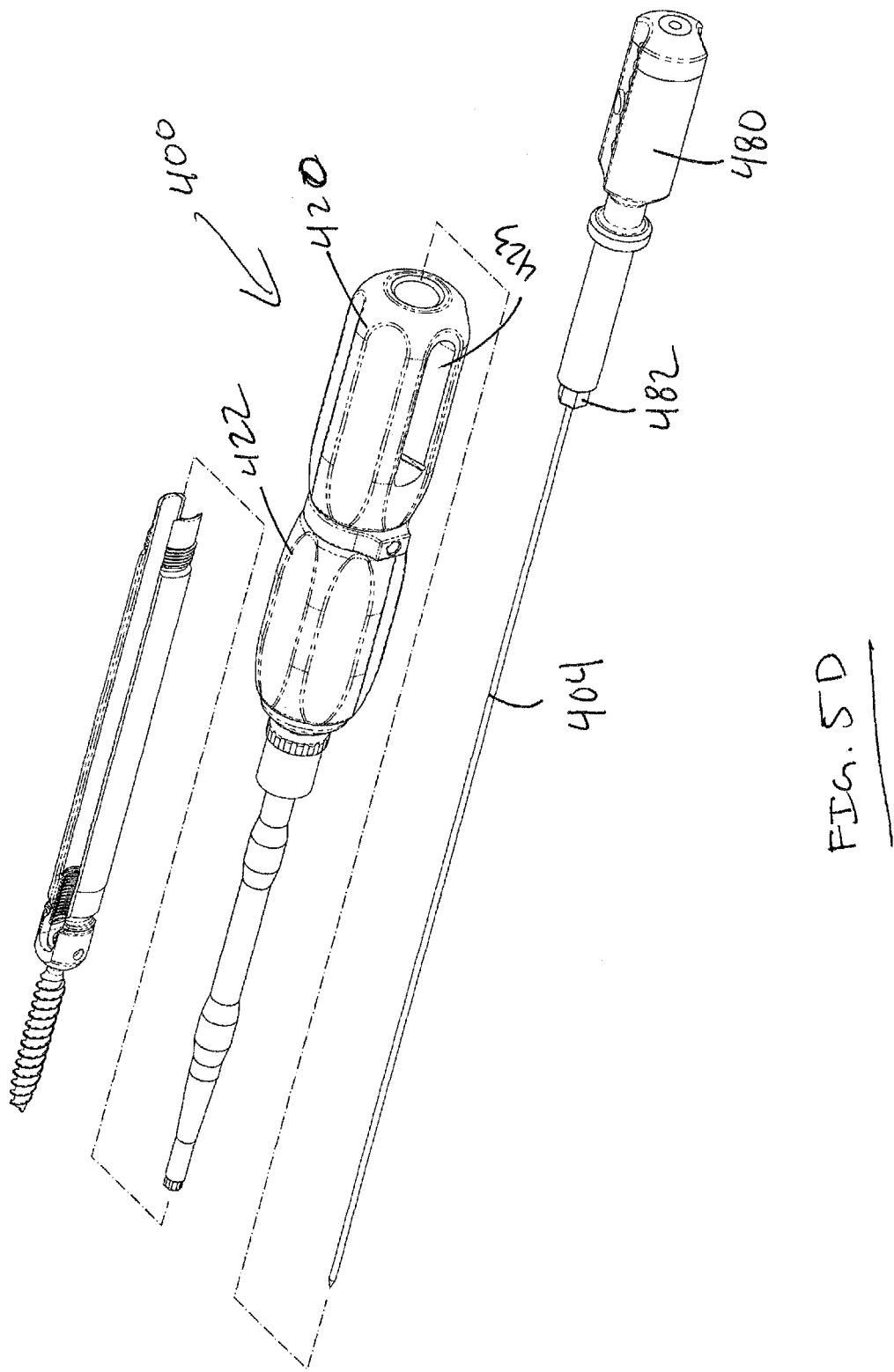
FIG. 5D is an exploded perspective view of the surgical instrument shown in FIGS. 5A-5C having a stylet with a positioning handle.

FIG. 5D illustrates an embodiment of tool that can be used to adjust a position of the stylet and to move the stylet holder between the first and second positions. A person skilled in the art will appreciate that the illustrated tool can be used with any of the devices described herein. As shown in FIG. 5D, the tool can include a positioning handle 480 that is configured to mate to a proximal end of the stylet 404. The positioning handle 480 can allow a user to advance the distal end of the stylet 404 through the stylet holder 460, such as when the stylet holder 460 is in the first position (i.e., the stylet 404 can translate relative to the stylet holder 460). In addition, the distal end of the positioning handle 480 can have a tool feature 482 (e.g., a protruding hex feature) that can engage the tool-engaging feature 466 of the stylet holder 460. As such, after advancing the stylet 404 through at least the stylet holder 460, the positioning handle 480 can engage the tool-engaging feature 466 of the stylet holder 460 and force the stylet holder 460 to rotate relative to the carrier 430 and form the second position with the carrier 430 (i.e., the stylet holder 460 rigidly engages the stylet 404).

As shown in FIGS. 5E-5G, the positioning handle 480 can include an outer body 484 encompassing at least a part of a positioning feature 486. The stylet 404 can extend from a distal end of the positioning feature 486 and out through a distal end of the outer body 484. The positioning feature 486 can include a push button 488 that can be depressed in order to disengage the positioning feature 486 from the outer body 484 and allow the positioning feature 486 and stylet 404 to translate relative to the outer body 484. As such, the positioning feature 486 can vary the length that the stylet 404 extends from the positioning handle 480, which can also vary the length of stylet 404 that can extend distally from the elongate shaft 402 (e.g., after the positioning handle 480 has coupled the stylet 404 to the stylet holder 460). Although described herein as a push button 488, any number of a variety of features for disengaging the positioning feature 486 from the outer body 484 can be used, such as, for example, a sliding or threaded feature.

In some embodiments, the push button 488 can engage the outer body 484 of the positioning handle 480 in a number of engagement positions 490. In addition, either the engagement positions 490 or the positioning feature 486 can include markings 492 that can inform a user as to the approximate length the stylet 404 extends from the elongate shaft 402 based on the type (e.g., length) of bone anchor attached (or to be attached) to the elongate shaft 402. For example, the outer body 484 can include a window 494 that reveals one of a plurality of markings (e.g., numbers) formed on the positioning feature 486. Each marking can correspond to a length of stylet 404 extending distally beyond a distal-most end of the elongate shaft 402. In addition, the markings can correspond to various bone anchor length to be used with the instrument to allow a user to select an appropriate bone anchor and adjust the stylet 404 relative to the elongate shaft 402 based on the selected bone anchor. For example, the user can select a 45 millimeter bone anchor to be implanted in a patient. The user can then set the positioning handle 480 (e.g., by pushing the push button 488 and moving the positioning feature 486) such that a marking (e.g., shown in the window 494) indicates that the stylet 404 is appropriately positioned relative to the elongate shaft 402 or bone anchor for a 45 millimeter bone anchor attached to the surgical instrument 400. In this position, a predetermined length (e.g., approximately 1 millimeter to approximately 30 millimeters) of the tip of the stylet 404 can extend distally beyond a distal-most end of the bone anchor mounted onto the elongate shaft 402.

In addition, after the stylet 404 has been initially positioned relative to the elongate shaft 402, the user can continue to observe the positioning of the stylet 404 relative to the elongate shaft 402 and bone anchor mounted thereon. For example, while not shown, in some embodiments, the stylet holder 460 can include a proximal extension that can include markings corresponding to the length of stylet 404 extending distally beyond the elongate shaft 402 or bone anchor. Additionally, the proximal handle 420 can include one or more viewing windows 423 that can allow a user to view the markings along the proximal extension of the stylet holder 460 in order to determine the length of stylet 404 extending from the distal end of the elongate shaft 402 or bone anchor. Although described herein as using markings, such as numbers, to indicate the stylet length to the user, any number of indicia, such as colors, pictures, etc., can be used.

In use, when the stylet holder 460 is in the first position (unlocked), the user can manipulate the positioning feature 486 to cause the stylet 404 to translate relative to the stylet holder 460 and along the elongate shaft 402, thereby adjusting a length of the stylet extending from a bone anchor assembly coupled to a distal end of the elongate shaft 402. Rotation of the positioning handle 480 can thread the stylet holder 460 into the carrier 430, thereby moving the stylet holder 460 to the second position (locked). The positioning handle 480 can be removed and the stylet 404 can be released from the positioning handle 480, such as due to a sliding or snap fit between the positioning handle 480 and stylet 404.

Figure 6A:
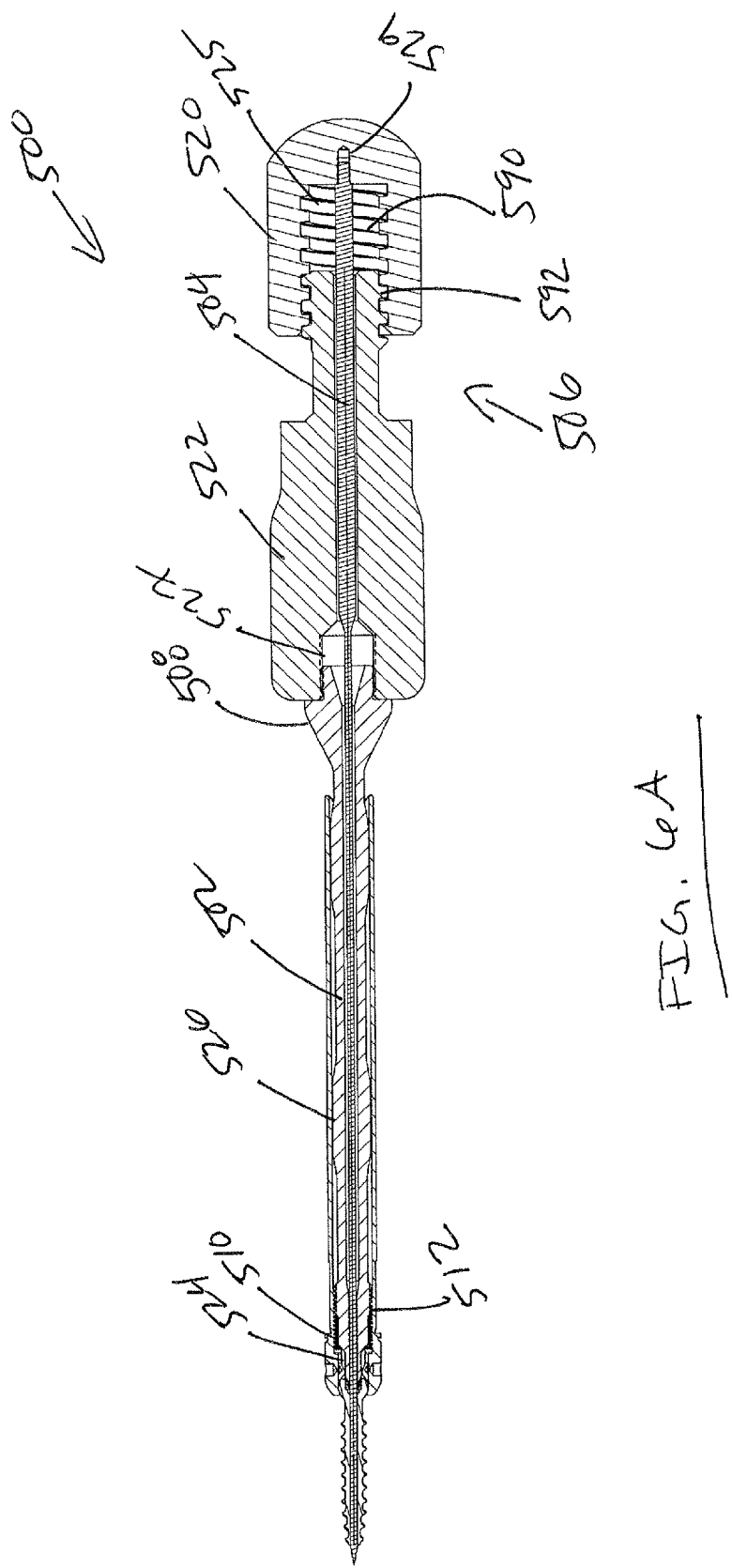
FIG. 6A is a cross-sectional view of another embodiment of a surgical instrument in a retracted position having a stylet coupled to a proximal handle, which can allow the stylet to be axially translated as a result of rotating the proximal handle relative to a distal handle of the surgical instrument.
Figure 6B:
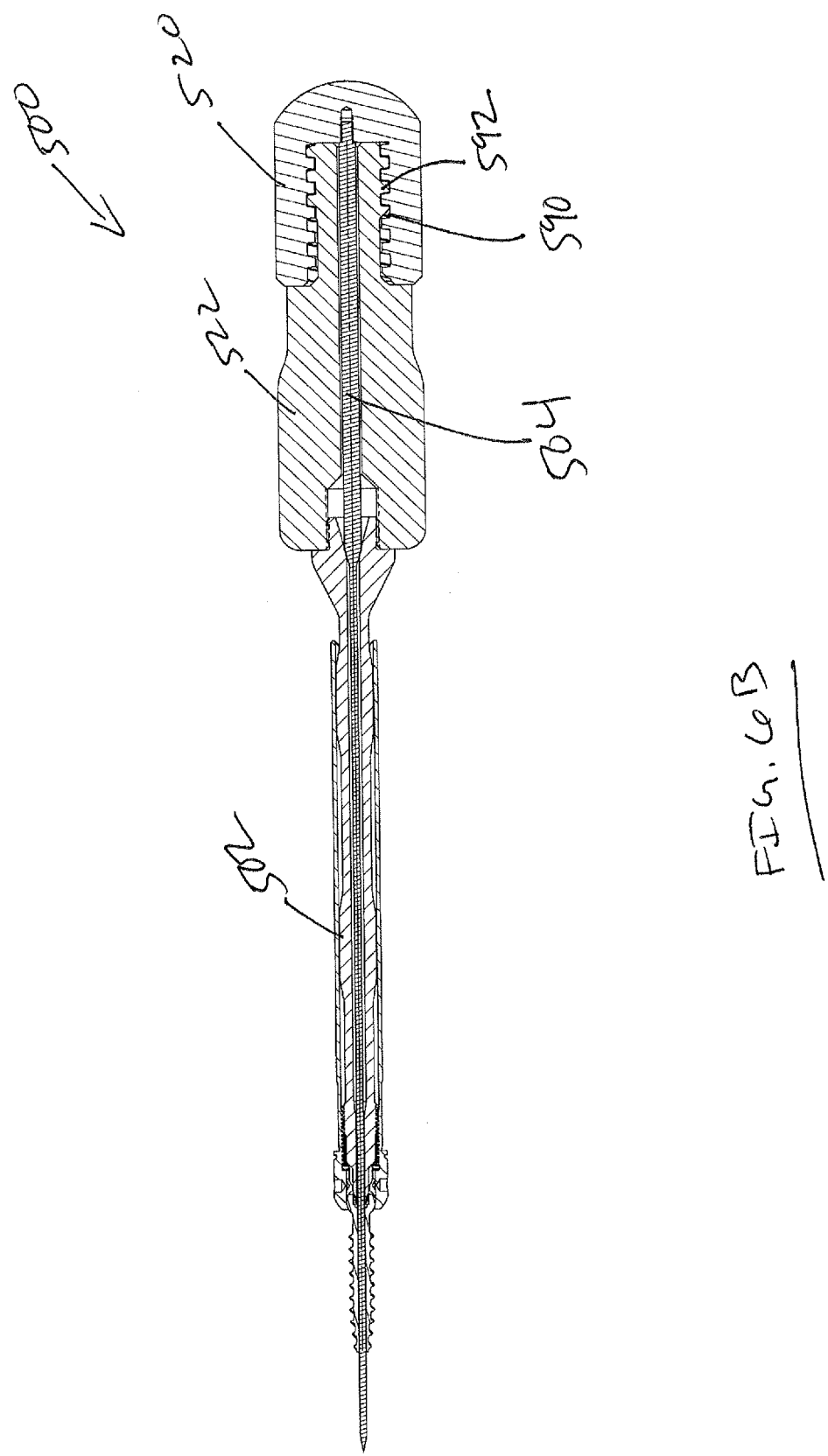
FIG. 6B is a cross-sectional view of the surgical instrument of FIG. 6A in an extended position.

FIGS. 6A and 6B illustrate another embodiment of a surgical instrument 500 for driving a bone anchor assembly into bone. The surgical instrument 500 can include an elongate shaft 502, a stylet 504, and a handle assembly 506. The elongate shaft 502 can have a proximal end 508 and a distal end 510, with a mating feature 512 formed on the distal end 510 and configured to mate to a bone anchor assembly. The elongate shaft 502 can be hollow with an inner lumen that can extend through and along the length of the elongate shaft 502. The stylet 504 can extend through at least a part of the elongate shaft 502, such as the inner lumen.

The handle assembly 506 can be coupled to a proximal end 508 of the elongate shaft 502 and can include a proximal handle 520 and a distal handle 522. The handle assembly 506 can be positioned and sized to allow a user, such as a surgeon, to grasp a part of the handle assembly 506 and operate the surgical instrument 500. In this embodiment, the handles are reversed as compared to prior embodiments. In particular, the proximal handle 520 controls a position of the stylet, whereas the distal handle 522 is used for driving a bone anchor assembly into bone.

As shown, the distal handle 522 is positioned between the proximal handle 520 and the proximal end 508 of the elongate shaft 502. The distal handle 522 has a proximal portion with a reduced diameter region that allows the proximal portion to be received within a bore 525 formed in the proximal handle 520. The proximal portion can include threads 592 formed on an external surface thereof that engage with corresponding threads 590 formed within the bore 525 extending proximally into a distal end of the proximal handle 520. The distal portion of the distal handle 522 is enlarged to facilitate grasping, and includes a bore 527 formed in a distal-most end thereof for receiving a proximal end 508 of the elongate shaft 502. As a result, rotation of the distal handle 520 relative to the proximal handle 520 will rotate the elongate shaft 502. As further shown, the bore 525 formed in proximal handle 520 includes a reduced diameter region 529 at a proximal-most end thereof for mating with a stylet 504. The stylet 504 can be threadably mated within the reduced diameter region 529, or otherwise fixedly mated thereto. As such, rotation of the proximal handle 520 relative to the distal handle 522 can translate the stylet 504 in a proximal or distal direction relative to the elongate shaft 502. Furthermore, rotation of the distal handle 522 can rotate the elongate shaft 502.

A mating feature 512 can be formed at the distal end 510 of the elongate shaft 502 and can be configured to engage a bone anchor assembly (e.g., bone anchor assemblies of the type described above with respect to FIGS. 1A-1B). The mating feature 512 can include a threaded surface configured to engage corresponding threads formed in the receiver membrane of the bone anchor assembly. The mating feature 512 can also include a tip 524 disposed distally of the threaded surface configured to engage a drive socket or a proximal surface of the bone anchor or a compression cap (not shown) disposed within the receiver member. The tip 524 can have a diameter that is less than the diameter of the threaded portion. The mating feature 512 can also be configured to engage a bone tap, or a bone tap can be formed integrally with the elongate shaft 502. One or more bulges 526 or areas of increase diameter can be formed along the length of the elongate body to engage and stabilize extension or protective sleeves that can be coupled to the bone anchor assembly.

In use, the stylet 504 can translate along a length of the inner lumen of the elongate shaft 502 and can extend out from the distal end 510 of the elongate shaft 502. In addition, translation of the stylet 504 along the inner lumen can allow the length of stylet 504 that extends from the distal end 510 of the elongate shaft 502, and in particular from a distal end of a bone anchor assembly coupled to the elongate shaft, to vary. For example, distal translation of the stylet 504 can allow the length of stylet extending from a bone anchor assembly to increase and proximal translation of the stylet 504 can allow the length of stylet 504 extending from a bone anchor assembly to decrease. When the proximal handle 522 is fully threadably engaged, as shown in FIG. 6B, the stylet is fully extended from the bone anchor assembly and is at its maximum length.

Figure 7:
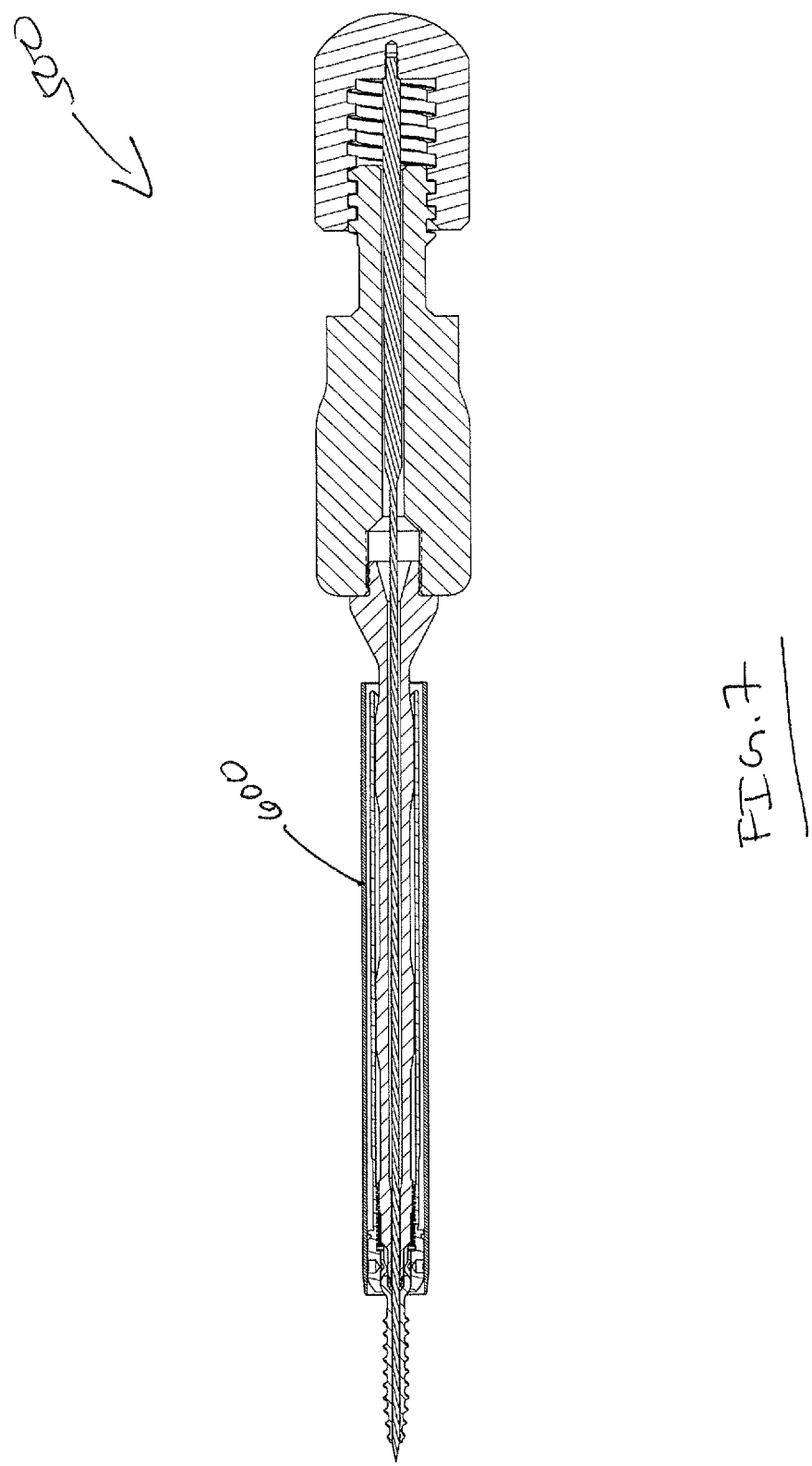
FIG. 7 is a cross-sectional view of a protective sleeve positioned over a part of the elongate shaft of the surgical instrument shown in FIGS. 6A and 6B.

FIG. 7 illustrates an embodiment of a protective sleeve 600 positioned over a part of an elongate shaft of a surgical instrument, such as the elongate shaft 502 of surgical instrument 500 described above and shown in FIGS. 6A and 6B. The protective sleeve 600 can assist with neurotransmitting procedures, such as neuromonitoring navigation. The protective sleeve can act as an insulator that can insulate at least the stylet. By way of non-limiting example the protective sleeve can be formed from one or more of a radio-opaque and radiolucent material, and can include radiopaque markers.

FIG. 8 illustrates another embodiment of a protective sleeve 600 positioned over a part of an elongate shaft of a surgical instrument, such as the elongate shaft 302 of surgical instrument 300 described above and shown in FIG. 4. Although the protective sleeve 600 is shown and described as being coupled to the surgical instruments 300 and 500 shown in FIGS. 7 and 8, any number of surgical instruments, including any disclosed herein, can be coupled with the protective sleeve 600.

Methods

The various instruments disclosed herein can be used to perform a variety of surgical procedures. While exemplary methods are discussed below for delivering a bone screw to a vertebra, a person skilled in the art will appreciate that the instruments can be used to deliver a variety of implants in various surgical procedures. By way of non-limiting example, the instruments can be used to deliver screws to soft tissue or bone throughout a patient's body, in minimally invasive, arthroscope, endoscopic, open, or other surgical procedures.

Figure 9A:
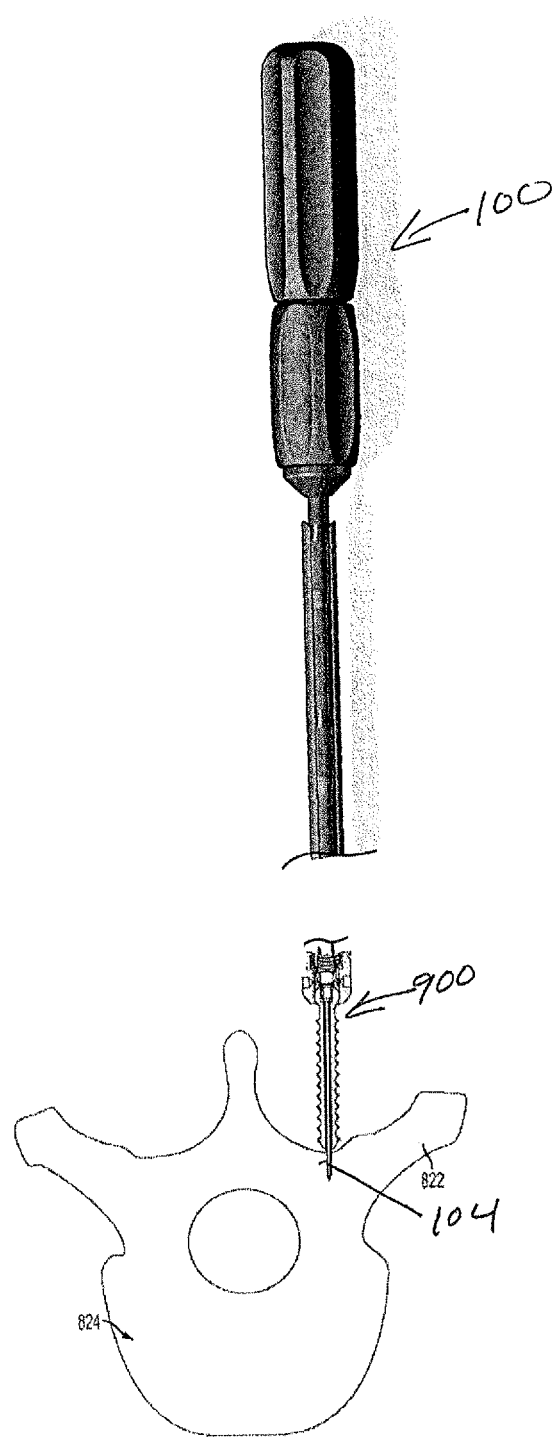
FIGS. 9A-9C schematically illustrate a method of using the surgical instrument of FIGS. 2A and 2B to drive a bone anchor assembly into bone.
Figure 9B:
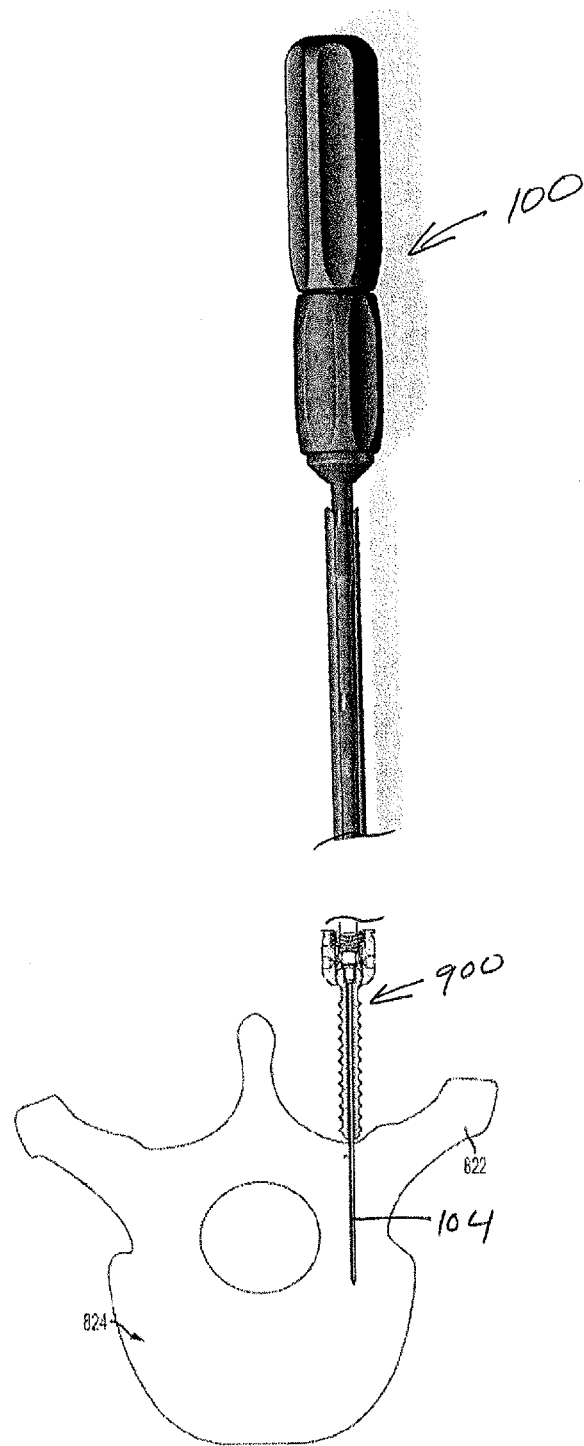
Figure 9C:
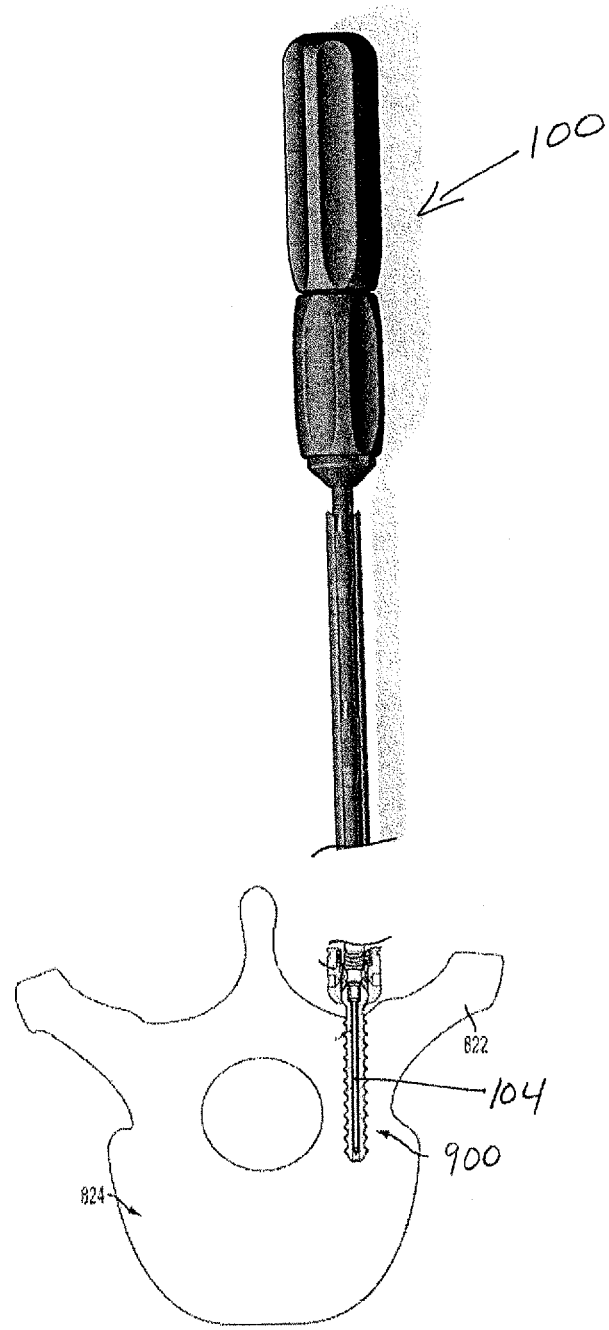

FIGS. 9A-9C schematically illustrate one exemplary methods of using a surgical instrument having a stylet to drive a bone anchor assembly into bone 824. The method detailed below can be used with any of the instruments disclosed above (e.g., the instruments 100, 200, 300, 400), with any necessary modifications being apparent to one skilled in the art having read the above disclosure. By way of example, the method is described in connection with instrument 100 of FIGS. 2A-2B.

To begin with, an incision can be made to access the bone 824 (e.g., a vertebra) to which the bone anchor assembly 900 (e.g., a pedicle screw) is to be coupled. The bone anchor assembly 900 can be coupled to the instrument 100 and advanced through the incision to position the bone anchor assembly in proximity to the bone surface. Prior to, during, or after insertion into through the incision, the stylet 104 can be indexed to an initial position based on various parameters such as the length of the bone anchor assembly. This can be accomplished, for example, by rotating the distal handle 122 while holding the proximal handle 120 fixed, to cause the carrier 130 and corresponding stylet 104 to translate axially. In other embodiments, for example using the instrument of FIGS. 4-5G, the stylet can be axially slid relative to the stylet holder prior to locking the stylet to the stylet holder. In some embodiments, the stylet 104 can be initially positioned such that the stylet 104 protrudes from the distal end of the bone anchor assembly 900 by a desired amount. This can be achieved, for example, using the positioning handle 480 (e.g., by pushing the push button 488 and moving the positioning feature 486) such that a marking (e.g., shown in the window 494) indicates that the stylet 404 is appropriately positioned relative to the elongate shaft 402. For example, the positioning handle 480 can be set to display a marking that corresponds to a length of the selected bone anchor, such that a predetermined portion of the tip of the stylet extending distally beyond a distal end of the bone anchor attached to the surgical instrument 400. The length can be further adjusted by adjusting the stylet relative to the carrier as may be desired. It will be appreciated that the stylet 104 can be initially positioned such that the stylet 104 does not protrude from the distal end of the bone anchor assembly 900.

As shown in FIG. 9A, the protruding stylet 104 can be docked into the pedicle 822 by tapping or urging the instrument distally towards the bone surface. The distal handle 122 can be rotated relative to the proximal handle 120, e.g., in a clockwise direction, in order to cause the stylet 104 to mechanically advance into the bone, as shown in FIG. 9B. Alternatively, or in addition, an impact force can be applied to the stylet 104 in the distal direction to advance the stylet 104 into the bone. The proper trajectory and depth can be confirmed with fluoroscopy. The insertion depth can also be inferred by the surgeon (e.g., based on the number of rotations of the distal handle 122, audible or tactile feedback, visual feedback provided by graduations or markings, such as shown through the viewing window 423 of the proximal handle 420, or based on the carrier hitting a stop disposed in or on the surgical instrument).

Once the stylet 104 is advanced to the desired depth, the proximal handle 120 can be rotated, e.g., in a clockwise direction, relative to the distal handle 122 (i.e., the distal handle 122 is held fixed) in order to drive the bone anchor assembly 900 along the path created by the stylet 104, as shown in FIG. 9C. Referring back to FIGS. 2A and 2B, rotation of the proximal handle 120 while holding the distal handle fixed 122 will cause corresponding rotation of the opposed tabs 136 on the proximal end of the elongate shaft 102. Since the carrier 130 is keyed to the tabs 136, the carrier 130 will be caused to rotate in coordination with the tabs 136. As a result, the threaded features 132 on the carrier will rotate relative to the threads 134 formed in the distal handle 122, which is held stationary. The carrier 130 will thus be forced to translate along the opposed tabs 136. Since the threads are reversed as compared to the threads on the bone screw, the carrier 130 will move proximally within the distal handle 122, thus moving the stylet 104 in a proximal direction relative to the bone screw 900. Since the stylet 104 is held fixed against the bone, the stylet 104 can be maintained at a constant depth within the bone as the bone anchor assembly 900 is advanced distally over the stylet 104. The handle assembly will move distally along the stylet 104 in coordination with distal advancement of the bone anchor assembly 900. In embodiments in which the threaded features of the carrier 130 and distal handle 122 have the same pitch as the threaded portion of the bone anchor assembly, retraction of the stylet 104 into the bone anchor assembly 900 can occur at the same rate as the advancement of the bone anchor assembly 900, such that the stylet 104 remains at a substantially fixed depth within the bone. In embodiments in which the threaded features of the carrier 130 and distal handle 122 have a smaller pitch than the threaded portion of the bone anchor assembly, retraction of the stylet 104 into the bone anchor assembly 900 can occur at a slight faster rate than advancement of the bone anchor assembly 900, such that the stylet 104 is at least partially retracted in a proximal direction relative to the bone as the bone anchor is driven into bone.

When the bone anchor assembly 900 is driven to the desired depth, the stylet 104 and the elongate body 102 can be detached from the bone anchor assembly and removed from the incision. Subsequent steps, such as affixing a spinal rod or other component to a receiver member of the bone anchor assembly can then be performed.

The bone anchor assembly can include various self-tapping features to facilitate insertion into the bone and to prevent the bone from fracturing during anchor insertion. In some instances, patient anatomy or surgeon preferences can require the bone to be tapped before inserting the bone anchor assembly. In such instances, the above method can be modified to use embodiments of the surgical instrument that include an integral bone tap or which are coupled to a bone tap via the engagement portion.

As discussed above, a tool can be used to adjust the position of a stylet of an instrument with respect to either an elongate shaft of the instrument or a bone anchor assembly coupled to the elongate shaft. As shown in FIGS. 5D-5G, the tool can include a positioning handle 480, which can be used to adjust the position of the stylet 404 relative to an elongate shaft, such as the elongate shaft 402 of the instrument 400 embodiment shown in FIGS. 5A-5D. Although the positioning handle 480 is described herein with respect to the instrument 400 embodiment shown in FIGS. 5A-5D, the positioning handle 480 can be used with any of the instrument embodiments.

Figure 10A:
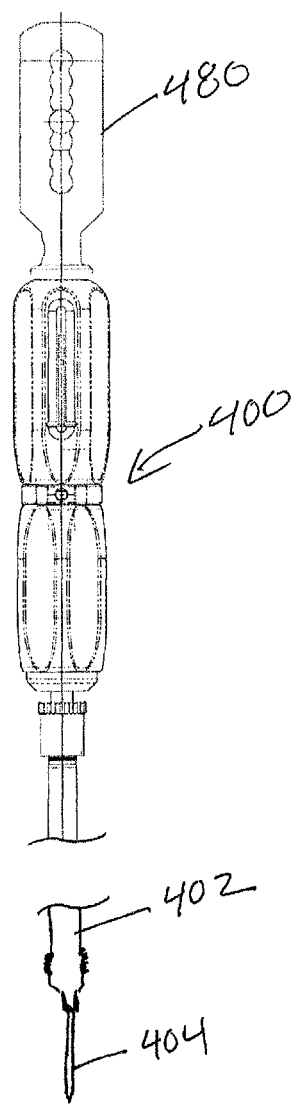

FIGS. 10A-10D schematically illustrate another exemplary method of using a tool or positioning handle 480 with the surgical instrument 400 having a stylet 404 to drive a bone anchor assembly 900 into bone 824. To begin with, a distal end of the positioning handle 480 can be removably coupled to a proximal end of the stylet 404, as shown in FIG. 10A. The length of stylet 404 extending from the elongate shaft 402 of the instrument 40 can be adjusted by pressing the push button 488 and sliding the positioning feature 486 in a distal direction (e.g., to increase the length) or proximal direction (e.g., to decrease the length). Once the stylet 404 length has been set (i.e., the push button is released and engages an engagement position 490), the user can engage the tool feature 482 at the distal end of the positioning handle 480 into the tool-engaging feature 466 of the stylet holder 460 in order to rotate the stylet holder 460. The stylet holder 460 can be rotated relative to the carrier 430 until the stylet holder 460 forms the second position with the carrier 430 where the stylet holder 460 rigidly engages the stylet 404 and locks the position of the stylet 404 relative to at least the stylet holder 460. The user can then remove the positioning handle 480 from the stylet 404 (e.g., pull the positioning handle 480 off the proximal end of the stylet 404).

The distal end of the instrument 400 can then be inserted into the incision and the distal end of the stylet 404 can be docked against the bone. The user can then apply a distally directed force on the proximal end of the instrument 400 in order to force the stylet 404 into the bone. Alternatively or in addition, the user can hold the proximal handle 420 and rotate the distal handle 422 in order to force the stylet 404 in the distal direction and into the bone. Once a desired length of stylet 404 has engaged the bone, the user can then rotate the proximal handle 420 in order to drive the bone anchor assembly 900 into the bone.

Figure 10C:
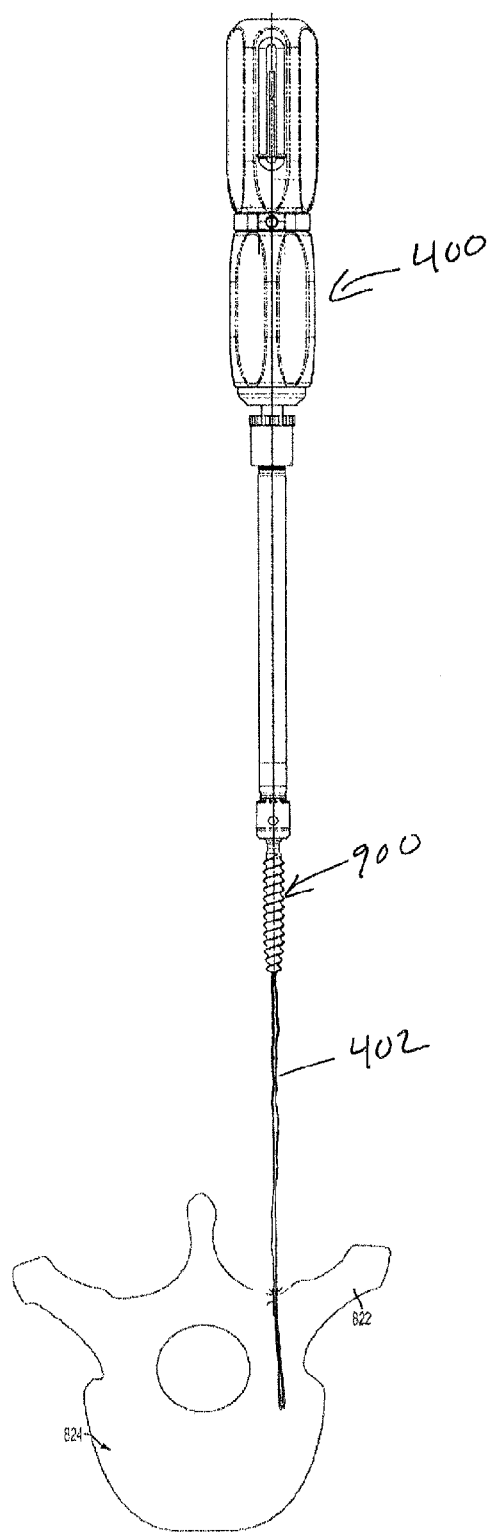

Alternatively, the bone anchor assembly 900 may not have been attached to the distal end of the elongate member 402 prior to insertion of the distal end of the instrument into the incision. A tool (e.g., having a protruding hex feature) can be inserted into the tool-engaging feature 466 (e.g., having a recessed hex feature) of the stylet holder 460 in order to rotate the stylet holder 460 relative to the carrier 430 and position the stylet holder 460 in the first position. As described above, when the stylet holder 460 is in the first position, the stylet 404 can move relative to the stylet holder 460. Therefore, the stylet 404 can remain in place (e.g., inserted into the bone) and the remainder of the surgical instrument 400 can be slid off the proximal end of the stylet 404, as shown in FIG. 10B. Such a configuration allows various other procedures to be performed at the surgical site without interference from the instrument 400, while at the same time maintaining the position of the stylet. Once the site is ready for anchor implantation, a user can attach a bone anchor assembly 900 onto the distal end 410 of the elongate member 402. Once the bone anchor assembly 900 is attached, the user can lead the proximal end of the stylet 404 through the distal end of the bone anchor assembly 900 and continue to advance the surgical instrument along the stylet 404 until the distal end of the bone anchor assembly 900 is in contact with the bone, as shown in FIGS. 10C and 10D. The stylet holder 460 can then be re-positioned into the second position (e.g., using the tool) in order to secure the stylet 404 to the stylet holder 460. The user can then proceed with driving the bone anchor assembly 900 into the bone over the stylet 404 (e.g., rotating the proximal handle 420), as described above.

When the bone anchor assembly is driven to the desired depth, the stylet 404 and the elongate body 402 can be detached from the bone anchor assembly 900 and removed from the incision. Subsequent steps, such as affixing a spinal rod or other component to a receiver member of the bone anchor assembly 900 can then be performed.

It should be noted that any ordering of method steps implied by the drawings or description herein is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

The stylet of the various embodiments disclosed herein can be rigid or flexible. The stylet can be formed from a radiopaque material to facilitate visualization under fluoroscopy and other imaging techniques. Other components of the devices disclosed herein (e.g., elongate body portions, handle portions, and the like) can be formed from a radiolucent material so as not to interfere with visualization of the guide projection. Exemplary radiolucent materials include carbon fiber and high-strength polymers. The devices disclosed herein can also be compatible with image-guide surgical systems and with stimulation systems (e.g., neuro-monitoring systems typically used to monitor for pedicle breach and to confirm screw or instrument placement).

The methods and devices disclosed herein can provide a number of advantages. For example, in some embodiments, the time required to target and place the bone anchor assembly can be reduced, the radiation exposure to the patient and to the surgical staff can be reduced, and procedural steps such as needle placement, guidewire insertion and removal, and tapping can be eliminated. By way of further example, in some embodiments, inadvertent advancement of instrumentation can be eliminated by controlling the guide projection depth throughout the procedure, risk of removing a guidewire during removal of a needle or tap can be eliminated, and bending or kinking of a guidewire can be prevented.

The devices and methods disclosed herein can be used in minimally-invasive surgery and/or open surgery. While the devices and methods disclosed herein are generally described in the context of advancing a bone anchor into a pedicle, it will be appreciated that the methods and devices disclosed herein can be used with any human or animal bone, implant, non-living object, and so forth.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. An instrument for driving a bone anchor assembly into bone, comprising:
   an elongate shaft having a distal tip configured to couple to a bone anchor assembly;
   a handle assembly coupled to a proximal end of the shaft and including first and second handles rotatably coupled to one another;
   a stylet extending through an inner lumen of the handle assembly and the elongate shaft; and
   a carrier entirely disposed within the handle assembly, wherein rotation of the first handle while the second handle is held stationary causes the carrier to non-rotatably translate axially relative to the elongate shaft in a proximal direction through the handle assembly to move the stylet proximally and causes rotation of the elongate shaft to drive the bone anchor assembly into bone.

2. The instrument of claim 1, wherein rotation of the second handle while the first handle is held stationary causes the carrier to rotatably translate relative to the first handle.

3. The instrument of claim 2, wherein the first handle is positioned distal to the second handle.

4. The instrument of claim 1, wherein the carrier is configured to rotatably translate relative to and within the handle assembly to adjust a longitudinal position of the stylet relative to the elongate shaft.

5. The instrument of claim 1, further comprising a stylet holder coupled to the carrier and releasably engaged to the stylet, the stylet holder allowing axial translation of the stylet therethrough when the stylet holder is in a first position relative to the carrier, and the stylet holder preventing axial translation of the stylet therethrough when the stylet holder is in a second position relative to the carrier.

6. The instrument of claim 1, further comprising a bone anchor assembly matable to the distal tip of the elongate shaft and having threads formed thereon that define an insertion rate of the bone anchor assembly into bone, and wherein the carrier is configured to translate within the handle assembly at a rate that is equal to the insertion rate of the bone anchor assembly.

7. An instrument for driving a bone anchor assembly into bone, the instrument comprising:
an elongate shaft having a proximal and distal ends, a mating feature formed on the distal end and configured to mate to a bone anchor assembly, and an inner lumen extending through the elongate shaft;
a stylet extending through the inner lumen of the elongate shaft; and
a handle assembly coupled to the elongate shaft, the handle assembly including
a proximal handle configured to rotate the elongate shaft to drive a bone anchor assembly coupled to the mating feature on the distal end of the elongate body into body,
a distal handle rotatable relative to the proximal handle, and
a carrier threadably and entirely disposed within the handle assembly and configured to move axially relative to the elongate shaft in response to rotation of one of the proximal and distal handles relative to the other one of the proximal and distal handles to cause the stylet to translate axially relative to the elongate shaft.

8. The instrument of claim 7, wherein rotation of the proximal handle while the distal handle is held stationary causes rotation of the elongate shaft, and rotation and axial translation of the carrier within the handle assembly.

9. The instrument of claim 7, wherein rotation of the distal handle while the proximal handle is held stationary causes the carrier to translate axially within the handle assembly without rotating the elongate shaft.

10. The instrument of claim 7, wherein the proximal handle is mated to the proximal end of the elongate shaft, and the distal handle is rotatably disposed about a proximal portion of the elongate shaft at a location distal to the proximal handle.

11. The instrument of claim 7, wherein the carrier is threadably coupled to threads formed within the distal handle.

12. The instrument of claim 7, wherein the stylet is integrally formed on and extends distally from the carrier.

13. The instrument of claim 7, wherein the stylet is removably mated to the carrier by a mating element.

14. The instrument of claim 7, further comprising a stylet holder disposed within the handle assembly and having the stylet extending therethrough.

15. The instrument of claim 14, wherein the stylet holder has a first position, in which the stylet is freely slidable relative to the stylet holder, and a second position in which the stylet holder rigidly engages the stylet to prevent movement of the stylet relative to the stylet holder.

16. The instrument of claim 15, wherein the stylet holder is configured to be advanced into the carrier to cause the stylet holder to move from the first position to the second position.

17. The instrument of claim 16, wherein the stylet holder includes a clamping feature that is compressed by the carrier in the second position to cause the clamping feature to rigidly engage the stylet.

18. The instrument of claim 7, wherein the elongate shaft includes a proximal portion with at least one slot extending therealong, the proximal portion extending through the distal handle and having a proximal end mated to the proximal handle.

19. The instrument of claim 18, wherein the carrier is slidably disposed within the proximal portion, and the carrier is non-rotatable relative to the proximal portion such that the carrier and the elongate shaft rotate together.

20. The instrument of claim 18, wherein the carrier includes one or more threaded features that extend through the at least one slot, the at least one slot allowing translation while preventing rotation of the carrier within the proximal portion of the elongate shaft.

21. The instrument of claim 7, further comprising a protective sleeve removably disposed around the elongate shaft.

22. The instrument of claim 7, further comprising a positioning handle coupled to a proximal end of the stylet that is configured to adjust a length of stylet that extends from a bone anchor assembly coupled to the distal end of the elongate shaft.

23. The instrument of claim 22, wherein the positioning handle includes a tool feature for engaging a stylet holder disposed within the handle assembly and having the stylet extending therethrough, the tool feature being configured to advance the stylet holder into the carrier to cause the stylet holder to move from a first position to a second position, wherein the second position locks the stylet to the stylet holder.

24. The instrument of claim 23, wherein the positioning handle includes an outer housing encompassing at least a part of a positioning feature that secures the proximal end of the stylet to the positioning handle.

25. The instrument of claim 24, wherein the positioning feature includes a push button that releasably engages an engagement position along the outer housing, the positioning feature being configured to move with the stylet relative to the outer housing when the push button is disengaged from the engagement position.

26. An instrument for driving a bone anchor assembly into bone, the instrument comprising;
an elongate shaft having a proximal and distal ends, a mating feature formed on the distal end and configured to mate to a bone anchor assembly, and an inner lumen extending through the elongate shaft;
a handle assembly coupled to the elongate shaft, the handle assembly including
a distal handle coupled to the proximal end of the elongate shaft and configured to rotate the elongate shaft to drive a bone anchor assembly coupled to the mating feature on the distal end of the elongate body into bone,
a proximal handle threadably coupled to the distal handle and coupled to a proximal end of a stylet that extends through the inner lumen of the elongate shaft, the proximal handle being rotatable relative to the distal handle to cause the stylet to axially translate relative to the elongate shaft; and a carrier entirely disposed within the handle assembly, the carrier being configured to translate relative to the elongate shaft in a proximal direction through the handle assembly to move the stylet proximally in response to rotation of the proximal handle.

* * * * *